US005688761A

United States Patent [19]

Owen et al.

[11] Patent Number: 5,688,761
[45] Date of Patent: *Nov. 18, 1997

[54] CONVERTIBLE MICROEMULSION FORMULATIONS

[75] Inventors: Albert J. Owen, West Chester, Pa.; Seang H. Yiv, Wilmington, Del.; Ani B. Sarkahian, Bryn Mawr, Pa.

[73] Assignee: LDS Technologies, Inc., Boothwyn, Pa.

[*] Notice: The term of this patent shall not extend beyond the expiration date of Pat. No. 5,444,041.

[21] Appl. No.: 406,862

[22] PCT Filed: Oct. 15, 1993

[86] PCT No.: PCT/US93/09933

§ 371 Date: Jun. 8, 1995

§ 102(e) Date: Jun. 8, 1995

[87] PCT Pub. No.: WO94/08604

PCT Pub. Date: Apr. 28, 1994

Related U.S. Application Data

[63] Continuation-in-part of Ser. No. 963,326, Oct. 16, 1992, abandoned, which is a continuation-in-part of Ser. No. 885,202, May 20, 1992, Pat. No. 5,444,041, which is a continuation of PCT/US92/03086, Apr. 15, 1992, which is a continuation-in-part of Ser. No. 841,931, Feb. 25, 1992, abandoned, which is a continuation-in-part of Ser. No. 837,347, Feb. 14, 1992, which is a continuation-in-part of Ser. No. 687,691, Apr. 19, 1991, abandoned.

[51] Int. Cl.$^6$ ........................ A61K 9/107; A61K 38/16; A61K 39/00

[52] U.S. Cl. ........................ 514/2; 514/13; 514/12; 424/94.3; 424/193.1; 424/400

[58] Field of Search ........................ 514/2, 13, 12; 424/88, 400, 94.3, 3, 193.1

[56] References Cited

U.S. PATENT DOCUMENTS

| | | | |
|---|---|---|---|
| 962,956 | 10/1910 | Constantinides . | |
| 962,957 | 10/1910 | Constantinides . | |
| 3,083,142 | 3/1963 | Howell et al. | 167/78 |
| 3,100,178 | 8/1963 | McLean et al. | 167/78 |
| 3,149,036 | 9/1964 | Woodhour et al. | 167/78 |
| 3,438,782 | 4/1969 | Elenbogen et al. | 99/2 |
| 3,492,399 | 1/1970 | Prigal | 424/91 |
| 3,776,857 | 12/1973 | Lindner | 252/308 |
| 3,983,228 | 9/1976 | Woodhour et al. | 424/89 |
| 4,094,971 | 6/1978 | Chedid et al. | 424/92 |
| 4,104,403 | 8/1978 | Barker et al. | 424/61 |
| 4,122,158 | 10/1978 | Schmitt | 424/94.61 |
| 4,182,918 | 1/1980 | Asher et al. | 424/600 |
| 4,241,051 | 12/1980 | Christie et al. | 530/307 |
| 4,395,394 | 7/1983 | Wolff, III et al. | 424/88 |
| 4,460,692 | 7/1984 | Tellier et al. | 435/248 |
| 4,481,188 | 11/1984 | Apontowell et al. | 424/89 |
| 4,650,677 | 3/1987 | Roerink | 424/89 |
| 4,690,774 | 9/1987 | Vishnupad et al. | 252/309 |
| 4,692,433 | 9/1987 | Hostetler et al. | 514/12 |
| 4,711,902 | 12/1987 | Serno | 514/356 |
| 4,719,239 | 1/1988 | Muller et al. | 514/785 |
| 4,720,353 | 1/1988 | Bell | 252/309 |
| 4,731,384 | 3/1988 | Dell et al. | 514/658 |
| 4,781,914 | 11/1988 | Deckner | 424/59 |
| 4,797,273 | 1/1989 | Linn et al. | 424/59 |
| 4,803,070 | 2/1989 | Cantrell et al. | 424/92 |
| 4,806,350 | 2/1989 | Gerber | 424/92 |
| 4,806,352 | 2/1989 | Cantrell | 424/92 |
| 4,914,084 | 4/1990 | Ecanow | 514/6 |
| 4,931,210 | 6/1990 | Takahashi et al. | 514/558 |
| 4,963,367 | 10/1990 | Ecanow | 424/485 |
| 4,980,084 | 12/1990 | Vishnupad et al. | 514/942 |
| 5,002,771 | 3/1991 | Purkaystha et al. | 424/433 |
| 5,026,825 | 6/1991 | Grebow et al. | 530/307 |
| 5,036,045 | 7/1991 | Thorner | 514/12 |
| 5,036,108 | 7/1991 | Asahi et al. | 514/937 |
| 5,037,653 | 8/1991 | Dawson | 424/405 |
| 5,045,337 | 9/1991 | El-Nokaly et al. | 426/602 |

(List continued on next page.)

FOREIGN PATENT DOCUMENTS

| | | |
|---|---|---|
| 0135171 | 3/1985 | European Pat. Off. . |
| 0274870 | 12/1987 | European Pat. Off. . |
| 0257368 | 2/1988 | European Pat. Off. . |
| 0278660 | 2/1988 | European Pat. Off. . |
| 0429248 | 11/1990 | European Pat. Off. . |
| 0314689 | 4/1992 | European Pat. Off. . |
| 3919982 | 6/1989 | Germany . |
| 53-50316 | 5/1978 | Japan . |
| 61185332 | 8/1986 | Japan . |
| 1171125 | 11/1969 | United Kingdom . |
| 2098865 | 12/1982 | United Kingdom . |
| WO 86/02264 | 10/1985 | WIPO . |
| WO 88/00059 | 1/1988 | WIPO . |
| WO 93/02664 | 2/1993 | WIPO . |
| WO 93/02665 | 2/1993 | WIPO . |
| WO 93/06921 | 4/1993 | WIPO . |
| WO 94/08603 | 4/1994 | WIPO . |
| WO 94/08605 | 4/1994 | WIPO . |
| WO 94/08610 | 4/1994 | WIPO . |

OTHER PUBLICATIONS

Charman, S. et al., "Self-Emulsifying Drug Delivery Systems: Formulaiton and Biopharmaceutic Evaluation of an Investigational Lipophilic Compound", *Pharmaceutical Research* 1992, 9(1), 87–93.

(List continued on next page.)

*Primary Examiner*—Cecilia J. Tsang
*Assistant Examiner*—Anish Gupta
*Attorney, Agent, or Firm*—Woodcock Washburn Kurtz Mackiewicz & Norris LLP

[57] ABSTRACT

There is provided a water-in-oil (w/o) micro emulsion which readily converts to an oil-in-water (o/w) emulsion by the addition of aqueous fluid to the w/o microemulsion, whereby an water-soluble biologically-active material in the aqueous phase is released for absorption by the body. The w/o microemulsion contains a preferred high purity short chain monoglyceride surfactant. The w/o microemulsion is particularly useful for storing proteins and the like for ling periods of time at room temperature and above until they are ready for use, at which time the addition of aqueous fluid converts the microemulsion to an o/w emulsion and release the protein.

22 Claims, 5 Drawing Sheets

U.S. PATENT DOCUMENTS

| | | | |
|---|---|---|---|
| 5,064,653 | 11/1991 | Session et al. | 424/404 |
| 5,084,289 | 1/1992 | Shin et al. | 424/439 |
| 5,110,606 | 5/1992 | Geyer et al. | 424/489 |
| 5,206,219 | 4/1993 | Desai | 514/3 |
| 5,444,041 | 8/1995 | Owen et al. | 514/2 |

OTHER PUBLICATIONS

Engstrom, L., "Aggregation and Structural Changes in the L2-Phase in the System Water/Soybean Oil/Sunflower Oil Monoglycerides", *J. Dispersion Science and Technology* 1990, 11(5), 479–489.

Engstrom, S. et al., "Enzyme Stabilization in Composite Cubic Phases", *Annals New York Academy of Sciences* 1990, 613, 429–30.

Engstroem, S., "Cubic Phases as Drug Delivery Systems", *Am. Chem. Soc., Div. Polym. Chem.* 1990, 31(2), 157–158.

Fletcher, P. and Parrott, "The Partitioning of Proteins between Water-in-oil Microemulsions and Conjugate Aqueous Phases", *J. Chem. Soc., Faraday Trans. 1*, 1988, 84(4), 1131–1144.

Fiedler, H.P., "Index of Auxiliary Substances", *Pharm. Ind.* 1989, 12, 1446–1449.

Friberg, S. and Mandell, "Phase Equilibria and Their Influence on the Properties of Emulsions", *J. of the Am. Oil Chemists' Society* 1970, 47, 149–152.

Ganguly, R. and Waldman, "Active and Passive Immunization", in Fundamentals of Immunology and Allergy, Lockey and Bukantz, ed., W.B. Saunders Company, Philadelphia, 1987, pp. 243–259.

Gulik-Krzywicki, T. and Larsson, "An Electron Microscopy Study of the L2-Phase (Microemulsion) in a Ternary System: Triglyceride/Monoglyceride/Water", *Chemistry and Physics of Lipids* 1984, 35, 127–132.

Kale, N. and Allen, "Studies on Microemulsions Using Brij 96 as Surfactant and Glycerin, Ethylene Glycol and Propylene Glycol as Cosurfactants", *Int. J. of Pharmaceutics* 1989, 57, 87–93.

Kemken, J. et al., "Influence of Supersaturation on the Pharmacodynamic Effect of Bupranolol After Dermal Administration Using Microemulsions as Vehicle", *Pharmaceutical Research* 1992, 9(4), 554–558.

"Kirk-Othmer Encyclopedia of Chemical Technology", 3rd Ed, vol. 8, pp. 908, 913–918, 929, John Wiley & Sons, New York, 1979.

Larsson, K., "Emulsions of Reversed Micellar Phases and Aqueous Dispersions of Cubic Phases of Lipids", *Am. Chem. Soc.* 1991, 45–50.

Luisi, P.L. et al., "Reverse Micelles as Hosts for Proteins and Small Molecules", *Biochim. Biophys. Acta* 1988, 947, 209–246.

Muller, B.W. and Kleinebudde, "Investigations of So-Called Microemulsion Systems. Part 1: Investigations of Drug-Free Systems", *Pharm. Ind.* 1988, 50(3), 370–375.

Muller, B.W. and Kleinebudde, "Investigations of So-Called Microemulsions. Part 2: Investigations of Drug-Containing Systems", *Pharm. Ind.* 1988, 50(11), 1301–1306.

Overkamp, D. et al., "Production of Polyclonal Antibodies in Ascitic Fluid of Mice: Technique and Applications", *J. of Immunoassay* 1988, 9(1), 51–68.

Pilman, E. et al., "Inverse Micellar Phases in Ternary Systems of Polar Lipids/Fat/Water and Protein Emulsification of Such Phases to Water/Oil/Water-Microemulsion-Emulsions", *J. Dispersion Science and Technology* 1980, 1(3), 267–281.

Ritschel, W.A., "Microemulsion for Improved Peptide Absorption from the Gastrointestinal Tract", *Meth. Fund. Exp. Clin. Pharmacol.* 1991, pp. 205–220.

Rizzo, V., "Hydrophilic Molecules Solubilized in Water-in-Oil Microemulsions: Distribution of Species in a Chemical Equilibrium", *J. of Colloid and Interface Science* 1986, 110(1), 110–113.

Thompson, K. and Gierasch, "Conformation of a Peptide Solubilizate in a Reversed Micelle Water Pool", *J. Am. Chem. Soc.* 1984, 106, 3648–3652.

Pouton, C.W., "A Study of Self-Emulsifying Oil/Surfactant Mixtures", Dept. of Pharmacy, Chelsea College, University of London, Jan. 1982, pp. 1–252.

Wakerly, M.G., "Self-Emulsifying Drug Delivery Systems Based on Nonionic Surfactant-Oil Mixtures", University of Bath, 1989.

"Oral Delivery of a Resin Inhibitor Compound Using Emulsion Formulations", *Pharmaceutical Research* 1992, 9(7).

OIL: CAPTEX 200
SURFACTANT: (CAPMUL; CENTROPHASE; TWEEN)(46:10.6:43.4)
AQUEOUS: 0.9% NaCl

■ MIN Aq %(w/w)
○ MAX AQ %(w/w)

OIL: CAPTEX 200
SURFACTANT: (CAPMUL: CENTROPHASE: CREMOPHOR)(31.5:6:62.5)
AQUEOUS: 0.9% NaCl

MIN Aq % (w/w)

MAX AQ % (w/w)

OIL: WITEPSOL H-15
SURFACTANT: (CAPMUL:MYVEROL:TWEEN)(15.4:8.5:76.0)
AQUEOUS: 20% SORBITOL IN 0.9% NaCl(w/w)

■ MIN Aq%(w/w)
○ MAX AQ%(w/w)

OIL: MYVACET 9-45K
SURFACTANT: (CAPMUL: MYVEROL: CREMOPHOR)(45.5:5.2:49.2)
AQUEOUS: 0.9% NaCl

- ■ MAX AQ %(w/w)
- ○ MAX. MIN AQ %(w/w)
- △ MIN AQ %(w/w)
- × MIN. MIN AQ %(w/w)

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 1
        ( D ) OTHER INFORMATION: /note=N- acetyl-Cys ( i x ) FEATURE:
        ( A ) NAME/KEY: Disulfide-bond
        ( B ) LOCATION: 5
        ( D ) OTHER INFORMATION: /note=Penicillamine amide ( i x ) FEATURE:
        ( A ) NAME/KEY: Disulfide-bond
        ( B ) LOCATION: 1..5

( i x ) FEATURE:
        ( A ) NAME/KEY: Modified-site
        ( B ) LOCATION: 2
        ( D ) OTHER INFORMATION: /note=alpha-N-methyl-Arg ( x i ) SEQUENCE DESCRIPTION: SEQ ID NO:1:

Cys  Arg  Gly  Asp  Xaa
        1                            5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 1

-continued

```
      ( D ) OTHER INFORMATION: /note=N- acetyl-Cys ( i x ) FEATURE:
      ( A ) NAME/KEY: Disulfide-bond
      ( B ) LOCATION: 1..7

( i x ) FEATURE:
      ( A ) NAME/KEY: Modified-Site
      ( B ) LOCATION: 3
      ( D ) OTHER INFORMATION:
            / note="4,4'-Dimethylthiazolidine-5-carboxycylic acid"

( i x ) FEATURE:
      ( A ) NAME/KEY: Modified-Site
      ( B ) LOCATION: 4
      ( D ) OTHER INFORMATION:
            / note="para-aminomethylphenylalanine"

( x i ) SEQUENCE DESCRIPTION: SEQ ID NO:2:

Cys  Asn  Xaa  Xaa  Gly  Asp  Cys
       1                  5
```

CONVERTIBLE MICROEMULSION FORMULATIONS

This application is a 371 of PCT/US93/09933, filed 15 Oct. 1993.

FIELD OF THE INVENTION

This is a continuation-in-part of Ser. No. 963,326 filed Oct. 16, 1992, now abandoned which is a continuation-in-part of Ser. No. 885,202 filed May 20, 1992, now U.S. Pat. No. 5,444,041, which is a continuation of PCT application PCT/US92/03086 filed Apr. 15, 1992, which is a continuation-in-part of application Ser. No. 841,931, filed Feb. 25, 1992 now abandoned which is a continuation-in-part of application Ser. No. 837,347, filed Feb. 14, 1992, which in turn is a continuation-in-part of application Ser. No. 687,691, filed Apr. 19, 1991, now abandoned.

This invention relates to microemulsions, and methods of making and using the same. More particularly, it relates to certain unique microemulsion formulations which are phase reversible (i.e., "convertible" as defined below), methods for making and storing them, and their use in administering drugs, proteins, and like biologically-active materials, including therapeutically-active ones.

As used herein, the microemulsions of this invention are self-emulsifying stable dispersions of oil and water, stabilized by interfacial films of surface-active molecules. These microemulsions are also characterized by their small average particle sizes, generally less than about 0.1 micron, by their wide range of temperature stability, typically from about 5° C. to 50° C., and they appear to be thermodynamically-stable, i.e., stable indefinitely over this range. They are also relatively insensitive to the pH or ionic strength of the aqueous internal phase.

These microemulsions are further characterized in that they form spontaneously without the need of high shear equipment, as distinct from conventional emulsions (macroemulsions) which must be prepared by the input of significant amounts of energy, and which are thus subject to extremes of temperature, pressure, and shear, resulting in damage to the contents of the emulsion. For further discussion of these systems, see "Microemulsions," M. Kahlweit, *Science*, 240:617–621 (1988).

By the term "convertible" or "phase reversible", as used herein to describe the microemulsions of this invention, is meant a microemulsion formulation capable of being changed from a water-in-oil (w/o) system to an oil-in-water (o/w) system by the addition of water to the former, as described in further detail below.

Also, "conversion," as used herein, is intended to define in particular the reversal of a w/o emulsion to form an o/w emulsion, as distinct from the term "inversion", as used in the art, which describes principally the change of a w/o emulsion to a water-in-oil-in-water (w/o/w) formulation.

BACKGROUND OF THE INVENTION

The preparation and use of microemulsions in the formulation of drugs, proteins, and the like are known in the art. See, for example, U.S. Pat. No. 3,989,843, which discloses the application of microemulsions to medical formulations. Also, in *Eur. J. Biochem.*, Samama et al., 163(3):609–617 (Mar. 16, 1987) describe liver alcohol dehydrogenase in ionic w/o microemulsions, while Lee et al. describe the extraction of epoxide cyclase, using various ionic microemulsions, in *FEBS Lett.*, 244(2):347–50 (Feb. 27, 1989). In each case, however, there is no teaching or suggestion that these microemulsions are phase reversible.

U.S. Pat. Nos. 4,931,210; 4,857,506; 4,714,566; and 4,590,086, on the other hand, disclose methods of preparing water-in-oil emulsions which are then inverted to form well-known water-in-oil-in-water phase (w/o/w) emulsions. These complex preparations, however, are macroemulsion formulations requiring high shear energy to prepare, and the resulting product is a w/o/w emulsion which actually comprises a w/o emulsion mixed into an aqueous phase in such a way that the first internal aqueous phase does not mix with the second continuous aqueous phase.

Emulsion systems for delivery of lipophilic agents via oral, parenteral, or local cutaneous administration and for transdermal delivery of the polypeptide hirudin are disclosed in U.S. Pat. No. 4,719,239 to Muller et al. Microemulsion systems containing drugs having a good hydrophilic/lipophilic balance for transdermal delivery are disclosed in GB Application 2,098,865. These references fail to disclose the use of a water-in-oil microemulsion for the mucosal delivery of a water-soluble active agent, such as proteins and peptides.

Microemulsion systems for use as injection compositions are set forth in GB 1,171,125. The compositions disclosed are not directed towards increased uptake of a biologically active material and the use of monoglycerides as surfactants is not shown.

Emulsion systems have also been used as vaccine adjuvant systems, particularly water-in-oil emulsions. The strength of the immune response and the speed with which it is evoked can be modified by the nature of the liquid matrix of the vaccine. One widely-used example of such a system is Freund's adjuvant, which consists of paraffin oil and a surfactant, mannide mono-oleate. These adjuvant emulsions, due to their thermodynamic instability, must be emulsified with a solution containing the immunogen just prior to injection of the vaccine. In addition, the paraffin oil in the adjuvant can lead to inflammation of the injection site and formation of granulomas. These two effects are greatly enhanced if immune stimulators are also employed. The oil and immune stimulators are helpful, however, in that they stimulate immune response by enhancing the activity of macrophages. These macrophages engulf the emulsion droplets and process the immunogen at the site of the injection. It would, therefore, be beneficial to be able to produce a vaccine adjuvant system which has a prolonged stability and thus, a prolonged shelf life in its prepared microemulsion state, and which can be formulated with a biodegradable oil which would not stimulate granuloma production.

There is a continuing need for new and improved delivery systems for biologically active materials. Many of the therapeutic agents emerging from the biotechnology revolution, as well as some older drugs such as insulin and calcitonin, consist of large-molecule proteins. These drugs must now be injected into the patient because they are unable to survive the digestive process and do not readily pass through the mucosal lining of the gastrointestinal tract and enter the bloodstream. A new drug delivery system that would enable proteins to enter the bloodstream through, for example, the lining of the digestive system would be of great benefit.

Improved drug delivery systems could also provide much improved convenience for patients. For example, calcitonin is a generic peptide hormone used for treatment of osteoporosis and other diseases involving bone loss. Osteoporosis affects 24 million Americans, including ⅔ of the women past menopause. Currently, most calcitonin is delivered by injection. Calcitonin treatment for osteoporosis requires long-term administration with low but frequent doses of the drug. An oral or suppository formulation of calcitonin would offer great advantages to patients undergoing such treatments..

SUMMARY OF THE INVENTION

In accordance with the present invention, there is now provided a composition comprising a highly stable water-in-oil microemulsion containing biologically, including therapeutically, active water-soluble materials in its internal aqueous phase, which water-soluble materials are controllably releasable when needed just prior to administration by the ready conversion of the microemulsion into an oil-in-water emulsion by the addition of water to form a continuous aqueous phase.

The invention also relates to the preparation of such microemulsions and their use in the administration of biologically and therapeutically active water-soluble materials.

One embodiment of the present invention is directed towards stable, water-in-oil microemulsion compositions that contain (i) an oil phase that has at least one pharmaceutically acceptable oil; (ii) an aqueous phase that contains water; (iii) a biologically active material; (iv) a surfactant mixture having a combined HLB value of from about 7 to about 14. The surfactant mixture is made up of at least one surfactant having an HLB value below about 8, the low HLB surfactant, wherein the low HLB surfactant component has at least 80% by weight, preferably at least 90% by weight, and more preferably at least 95% by weight of a $C_9$, $C_{10}$, $C_{11}$, $C_{12}$, or $C_{13}$ monoglyceride or mixtures thereof. The surfactant mixture is also made up of at least one surfactant having an HLB value above about 8 which surfactant is referred to as the high HLB surfactant. The low and high HLB surfactant can be a mixture of different surfactants. Preferred low HLB surfactants include $C_9$, $C_{11}$, $C_{13}$ monoglycerides or mixtures thereof, more preferably $C_{11}$ or $C_{13}$ monoglycerides or mixtures thereof.

One aspect of the invention is the storage or maintenance of materials, such as proteins and peptides, in a solubilized state at temperatures or conditions at which they would otherwise be unstable. For example, it has been found that some proteins can be stored dissolved in the aqueous phase of the w/o microemulsions at temperatures at which the protein would be unstable if stored merely as an aqueous solution. Such proteins may be stored in a w/o microemulsion of this invention until ready to be used, at which time water is then added until an o/w emulsion has formed, which emulsion is then administered orally or by injection. Also, the stored w/o microemulsion can be administered to the body wherein it is converted to an o/w emulsion by the addition of body fluids. In this manner, storage problems are lessened or eliminated.

Typical of the storage times for drugs, proteins, and the like, which may be achieved with the compositions of this invention, are times anywhere from about 1 to 48 hours, preferably 16–24 hours up to several, i.e., 3–12, weeks or months, at temperatures of from about room temperature, i.e., about 20° C., up to the temperature where the microemulsion breaks, generally in the range of about 50°–70° C., preferably below about 40° C. Temperatures below room temperature such as about 4° C. can, of course, be used.

In a further aspect of this invention, it has been found that, unexpectedly, if a w/o microemulsion of this invention containing, for example, a water-soluble drug in the internal aqueous phase, is administered directly to the body of animals, including humans, the body fluids themselves are sufficient to convert the w/o microemulsion to an o/w emulsion, thereby slowly releasing the drug in situ. This is particularly advantageous over pre-conversion with water in that because body fluids are employed, the total volume of liquid administered is smaller. This method is particularly useful in administration into the colon or intestines of such drugs as peptides, proteins, or other molecules with bonds that are readily attacked by enzymes, where the oil protects the drug in the intestines until it is slowly released as the body fluids convert the emulsion. In the case of calcitonin, for example, if it is administered into the colon as just an aqueous solution, colon enzymes destroy the drug before it is absorbed, whereas with the microemulsion formulations of this invention, the calcitonin is protected from the enzymes until it is slowly released by hydration within the body.

In one particular embodiment of the present invention the w/o microemulsion system is formulated such that, upon conversion with additional water, an o/w microemulsion is formed. Such a system is advantageous in that the converted system has a small particle size. In another embodiment of the present invention, the microemulsion system is formulated as a solid at room temperature which has surprisingly been found to enhance drug uptake and activity for gastrointestinal delivery.

A particular embodiment of the present invention is the use of a w/o microemulsion as a vaccine adjuvant system. The immunogen is carried in the aqueous phase of the microemulsion adjuvant system, which when introduced into the body and contacted with aqueous body fluids, undergoes conversion to form an oil-in-water emulsion.

"Administration to the body", as used herein can be by any mode. Systems that convert to macroemulsions are preferably administered parenterally, enterally, or via any other mucous membrane, more preferably administration is either orally, rectally, or vaginally. Systems that convert to microemulsions are administered in the same modes as those that convert to macroemulsions, but are also preferably administered intravenously and intraarterially.

In yet another embodiment of this invention, it has been determined that these w/o microemulsions may also be used to formulate topical salves which are highly advantageous in that they remain moist on the skin for long periods of time without drying and crumbling.

DESCRIPTION OF THE INVENTION

Figure 1:
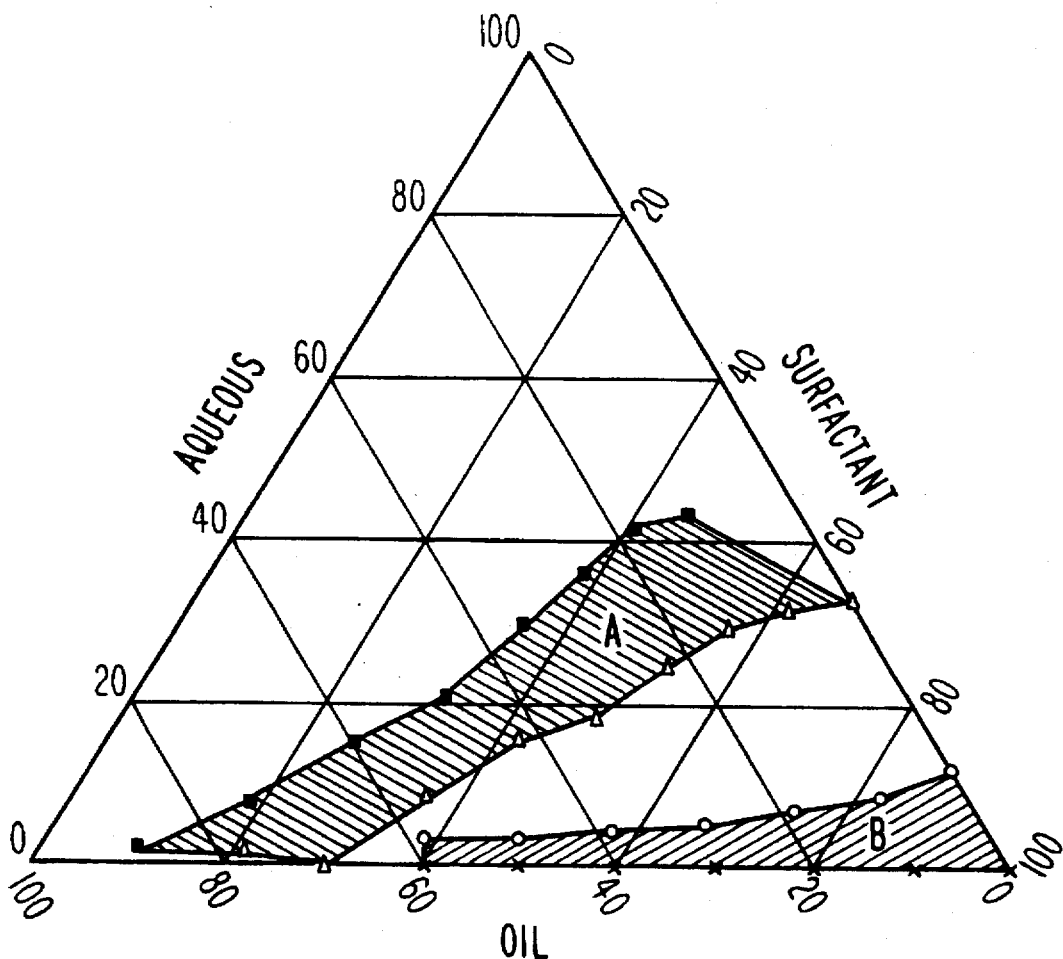
FIG. 1 is a phase diagram depicting the various microemulsion formulations existing using an oil phase consisting of Captex 200, Imwitor 308 as the low HLB surfactant, Tween 80 as the high HLB surfactant, and saline as the aqueous phase.

The production and use of water-in-oil (w/o) microemulsion compositions containing water-soluble biologically active materials has been described in copending application Ser. No. 885,202, filed May 20, 1992, which is incorporated in its entirety, assigned to the assignee of the present application. It has now been surprising found that the use of high purity $C_{9-13}$ monoglycerides as the low HLB (hydrophilic-lipophilic balance) surfactant enhances the uptake of the active material upon administration.

The water-in-oil microemulsion compositions of this invention which are capable of converting, upon addition of aqueous fluid, to an oil-in-water emulsion are produced by combining (1) an oil phase which contains at least one pharmaceutically acceptable oil; (2) an aqueous phase which contains water; (3) at least one biologically active material; (4) a mixture of surfactants having a combined HLB value of generally from about 7 to about 14, the surfactant mixture containing (i) at least one surfactant having an HLB value below about 8, referred to as the low HLB surfactant, and (ii) at least one surfactant having an HLB value above about 8, referred to as the high HLB surfactant. The low HLB surfactant includes at least 80 percent by weight, preferably at least about 90 percent by weight, and more preferably at least about 95 percent by weight, of a $C_9$, $C_{10}$, $C_{11}$, $C_{12}$, or $C_{13}$ monoglyceride or mixtures thereof. These monoglycerides have fatty acid moieties of from 6 to 10 carbon atoms bonded onto the 3 carbon glyceride backbone, thus they can also be referred to as $C_{6-10}$ fatty acid monoglycerides.

In addition, there may optionally be included into the w/o microemulsion such other adjuvants as stabilizers, coloring agents, oil soluble drugs and the like. Each of these components and adjuvants must be suitable for use in the subject and will usually be food grade and/or pharmaceutically-acceptable materials. Any drugs will be present in therapeutically-effective amounts. The compositions of the present invention are biologically compatible w/o microemulsions. These compositions are biologically compatible in that they are non-toxic and contain biodegradable or non-absorbable materials. By non-toxic it is meant non-toxic dependent upon the route of administration to a subject, in that the toxicity of one route may not be equivalent to that of another route.

The microemulsions of the present invention are created by the interplay between the surfactant or mixture of surfactants and the oil and aqueous phases. The surfactant or mixture of surfactants preferably have a hydrophilic-lipophilic balance (HLB) within a specified range. By "hydrophilic-lipophilic balance" is meant an empirical quantity, on an arbitrary scale, which is a measure of the polarity of a surfactant or mixture of surfactants. See P. Becher et al., "Nonionic Surfactant, Physical Chemistry," Marcel Dekker, N.Y. (1987), pages 439–456. It is a widely known and used term. The w/o microemulsions can be solids including semi-solids, gels, or liquids at room temperature.

More particularly, the amount of the components should be such that the biologically-active material comprises from $10^{-9}$ to 100 weight/volume %, based on the volume of the aqueous phase. Generally, in the microemulsion system, the aqueous phase ranges up to about 60 volume percent; the oil content ranges from about 5 to about 99, preferably from about 10 to about 99 volume percent; the surfactant content ranges from about 1 to about 70 volume percent.

The water content in the w/o microemulsions is up to about 20 volume percent, preferably up to about 30 volume percent, most preferably up to about 40 volume percent, and in some cases as high as 60 volume percent of the microemulsion. In a preferred high aqueous phase content w/o microemulsion system, the aqueous phase content ranges from about 20 to about 60 volume percent, preferably from about 30 to about 60%, most preferably about 40–50%; the oil content ranges from about 5 to about 60 volume percent, preferably from about 10 to about 50%, most preferably about 15–40%; the surfactant content ranges from about 5 to about 30 volume percent, preferably from about 5 to about 25%, more preferably about 5–20% for the low HLB surfactant; and from about 5 to about 30 volume percent, preferably from about 5 to about 25%, more preferably from about 10 to about 25%, for the high HLB surfactant.

In a preferred low aqueous phase content w/o microemulsion system, the aqueous phase should comprise no more than about 20%, preferably the aqueous phase content ranges from about 0.1 to about 20%, most preferably about 0.1–15% volume percent; the oil content ranges from about 35 to about 90 volume percent, preferably about 45–90%; the surfactant content ranges from about 5 to about 25 volume percent, preferably about 10–25% for the low HLB surfactant, and from about 1 to about 20 volume percent, preferably from about 1–15% for the high HLB surfactant. In general, when the aqueous phase of the w/o microemulsion is below about 20% volume, the ratio of oil phase to low HLB surfactant, is at least 1:1, preferably from 1:1 to about 15:1, more preferably from about 2:1 to about 10:1, and in some cases from about 2:1 to about 5:1.

The water component of the aqueous phase can be partially replaced by the incorporation of another polar, biologically compatible solvent such as polyhydrolic alcohols having at least 2 hydroxyl groups, glycerol, propylene glycol, and mixtures thereof. However, in general, the aqueous phase consists of at least 40%, preferably at least 60%, and more preferably at least 75%, by volume water. Thus, the term "aqueous phase" as used herein is intended to encompass a phase comprising water, such polar solvents, and mixtures thereof. The aqueous phase may comprise, in addition to water (or other polar solvent) and active material, such other adjuvants such as, but not limited to, stabilizers, coloring agents, modifiers, and the like, or salts (e.g., when saline is used).

The formulation of a microemulsion having a high aqueous phase content is preferred in those situations where the biologically-active material has a relatively low solubility in water or where a relatively high quantity of the biologically-active material is desired in the microemulsion system.

Adjuvants, such as preservatives, coloring agents, flavors or oil-soluble drugs, e.g., steroids, if any, should be included only in those amounts which will not adversely affect the novel properties of the microemulsion, generally in amounts of up to 20% by volume, based on the total volume of the composition.

In the following description it will be understood that the nature of the oils and surfactants is not critical beyond those particular qualifications set forth below, and may generally be any such known materials conventionally employed and which are accepted in the food and pharmaceutical industry. The oils or surfactants are considered to be "pharmaceutically acceptable" in that they are readily accepted by those of skill in the art as being safe for use in the mode of administration specified or intended. Thus, for example, such oils as propylene glycol diesters are safe for oral administration and such oils as triglycerides are safe for intravenous administration.

The oil, or mixtures thereof, may be liquid at room temperature, although in some cases, mild heating of a solid oil to form a liquid is acceptable. If injection is the preferred route of administration, the oil should be liquid at room temperature. Heating of an oil that is solid at room temperature is desirable for formulations intended as suppositories, creams, salves, and in some cases as oral capsules.

Illustrations of suitable oils for purposes of this invention include triesters of glycerol having from about 9 to 83, preferably 21–60, and more preferably 21–45 carbon atoms. The triglycerides are further defined as short chain triglycerides having 9–15 carbon atoms, medium chain triglycerides having 21–45 carbon atoms, and long chain triglycerides having above 45 carbon atoms. Short chain and medium chain triglycerides are preferred for liquid w/o microemulsion systems. Examples of glycerol triesters include natural, edible oils such as canola, corn, olive, sunflower and coconut oils, triacetin, the decanoic acid esters, and chemically-synthesized oils such as 1-oleyl-2,3-diacetyl glycerol. Commercially available triglyceride oils, both natural and chemically-synthesized, are available from Karlshamns Lipid Specialties, USA as the Caprex® series, and from Huls America Inc. as the Miglyol series.

Other suitable oils include diesters of propylene glycol having from about 7 to 55, preferably 15–40 carbon atoms, more preferably propylene glycol esters of capric and caprlic acids, and mixtures thereof, having from 19 to 23 carbon atoms. The diesters of propylene glycols are further defined as short chain having from 7–11 carbon atoms, medium chain having from 15–31 carbon atoms, and long chain having above 31 carbon atoms. Diesters of propylene glycols include propylene glycol esters of capric acid, caprylic acid, and mixtures thereof such as Captex® 200, and Caprex® 800 (Karlshamns Lipid Specialties, Columbus, Ohio) and other ester groups as described above for glycerol.

The surfactant, or more preferably, the mixture of surfactants, should be chosen from those having a resulting HLB value in the range of from about 7 to 14, more preferably 8 to 13. When a mixture of surfactants is employed, while some of the components may have a value outside the desired range, e.g., below about 5, it will be understood that by mixing in surfactants with HLB's greater than, e.g., about 9, the resulting combined HLB value will be in the range of 7 to 14. Although some protein and peptide delivery system compositions require the presence of certain surfactants, such as sterols and lecithin, the present w/o microemulsion compositions do not require the presence of such surfactants or mixtures thereof. The present invention, however, can be formulated with such surfactants, either in combination or alone. Beyond the requirement for the monoglyceride in the low HLB surfactant part of the w/o microemulsions, the microemulsion can be essentially free, that is containing less than about 0.05% wt. in the w/o microemulsion of any of the listed surfactants.

Surfactants which may be employed in our compositions include both ionic agents, i.e., cationic, anionic or zwitterionic, and non-ionic agents, or mixtures thereof. Examples of cationic surfactants include cetyldimethylethylammonium bromide, cetylpyridinium chloride and other salts of these surfactants.

Examples of anionic surfactants include $C_{8-32}$ fatty acids and salts thereof; cholic acid and derivatives thereof such as deoxycholate, and its salts, ursodeoxycholic acid, and taurocholic acid; $C_{8-56}$, diesters of tartaric acid; phospholipids such as phosphatidic acid and phosphatidyl serine; $C_{5-29}$ monoesters of lactic acid; $C_{8-20}$ sulfonates, including alkyl-, olefin-, and alkylaryl derivatives; tridecyl- and dodecylbenzene sulfonic acids; and $C_{5-33}$ sarcosine and betaine derivatives.

Zwitterionics include such phospholipids as lecithin, phosphatidylethanolamine, and sphingomyelins. The phospholipids are particularly preferred for use as both the low and high HLB surfactants.

Among the non-ionic surfactants which may be employed are ethoxylated castor oil; $C_{5-29}$ mono-glycerides and ethoxylated derivatives thereof; $C_{15-60}$ diglycerides and polyoxyethylene derivatives thereof having 1 to 90 POE groups; $C_{10-40}$ esters (10–40 carbon atoms in the alcohol) of long chain fatty acids(fatty acids having 16 carbon atoms and above); $C_{10-40}$ alcohols; sterols such as cholesterol, ergosterol, and $C_{2-24}$ esters thereof; $C_{8-96}$ ethoxylated fatty esters; $C_{14-130}$ sucrose fatty esters; and $C_{20-130}$ sorbitol and sorbitan monoesters, diesters, and triesters, and polyoxyethylene (POE) derivatives thereof having 0 to 90 POE groups, e.g., polyoxyethylene sorbitan monooleate, sorbitol hexaoleate POE (50). Of these, mono- and di-glycerides, or mixtures thereof, are preferred as low HLB surfactants and the sorbitol and sorbitan compounds as high HLB surfactants.

More specifically, preferred low HLB surfactants include $C_9$ to $C_{13}$ monoglycerides, $C_{19}$ to $C_{25}$ diglycerides of mono and poly unsaturated fatty acids, $C_{15}$ to $C_{23}$ diglycerides, and $C_{35}$ to $C_{47}$ diglycerides of mono and poly unsaturated fatty acids; preferred high HLB surfactants include ethoxylated castor oil, and the sorbitan surfactants. Short chain monohydroxyl alcohols, such as $C_1$ to $C_6$ are preferably not employed as surfactants in these systems due to toxicity factors.

The low HLB surfactant system employed in the w/o microemulsions of the present invention contains at least about 80 percent by weight, preferably at least about 90 percent by weight, and more preferably at least about 95 percent by weight, of a $C_9$, $C_{10}$, $C_{11}$, $C_{12}$, or $C_{13}$ monoglyceride or mixtures thereof, preferably a $C_9$, $C_{11}$, or $C_{13}$ monoglyceride or mixtures thereof, and more preferably a $C_{11}$ or $C_{13}$ monoglyceride or mixtures thereof. Commercial examples of these surfactants include Imwitor 308, manufactured by Muls America, Inc., having about 80–90% wt. $C_{11}$ monoglycerides; and Glycerol Monocaprylin, manufactured by Sigma Chemicals as 1-monooctanoyl-rac-glycerol having about 99% wt. $C_{11}$ monoglycerides, and Glycerol Monocaprate, manufactured as 1-monodecanoyl-rac-glycerol by Sigma Chemicals, having about 99% wt. $C_{13}$ monoglycerides. The low HLB Surfactant system can either be a combination of the preferred high purity $C_{9-13}$ monoglyceride surfactant with other low HLB surfactants, or the low HLB surfactant system can be comprised solely of the preferred high purity $C_{9-13}$ monoglyceride surfactant or mixtures thereof.

The active material to be incorporated into the w/o microemulsions is preferably water-soluble. The water-soluble active material of the w/o microemulsion may be any biologically active, preferably therapeutic, material, particularly water-soluble proteins, peptides and other pharmaceutically-active compounds, i.e., drugs, and compounds which may have use as diagnostic agents. Vitamins and other food supplements which are not commonly defined as being "therapeutic" are not within the definition of the active agent. Illustrations of proteins which may be advantageously formulated, particularly for prolonged storage, include enzymes, such as horseradish peroxidase, alkaline phosphatase and derivatives thereof; and other unstable proteins which tend to undergo inactivation during storage at elevated temperatures, such a cytokines, hemoglobin, interleukins, and the like. Peptides including polypeptide hormones such as calcitonins, insulins, and the like are suitable for incorporation.

Other active agents that can be used in the w/o microemulsion system include peptides which may be satisfactorily employed include such pharmaceutically-active peptide drugs as desmopressin (1-desamino-8-D-arginine vasopressin). Drugs that can be employed in this system are water soluble drugs which are characterized by having low oral bioavailability. Examples of some of the drugs that can be employed include: anticoagulants, such as heparin or its derivatives; antimicrobials, such as penicillin G, carbenicillin, meziocillin and other poorly absorbed penicillin derivatives; cephalosporins, such as cephalothin, cefoxitin, cefotaxime and other molecules in this series normally administered by injection; antineoplastic drugs, such as fluorouracil, cytarabine, azauridine, thioguanine, vinblastine, vincristine, and bleomycin; anti-inflammatories, such as aurothioglucose and gold sodium thiomalate; and antiparasitic drugs, such as suramin and mebendazole.

Other active agents include RGD peptides, hematoregulatory peptides, vasopressin, collagenase inhibitors, angiotensin inhibitors, mammalian growth hormones, erythropoeitins, interleukins (e.g. IL-2, 3, 4 and the like), clotting factors (e.g. factors VII, VIII, IX) colony stimulating factors (e.g. G-CSF, GM-CS, M-CSF), hypothalamic releasing peptides (e.g. growth hormone releasing peptides, gonadotropin releasing factors), interferons, tissue plasminogen activators, atrial natriuretic peptides, tumor necrosis factor, antibodies, antibody fragments, clotting factors, dismutases, vaccine, immunoregulators, HIV protease inhibitors, neurotrophic factors (e.g. nerve growth factors), peptide and protein mimetics, and angiotensin II antagonists.

The present invention also provides for formulations incorporating small peptides, from about 2 to about 10, more preferably from about 2 to about 6 amino acid moieties. One group in particular, the fibrinogen receptor antagonists (RGD containing peptides) are tetrapeptides with an average molecular weight of about 600. These peptide antagonists are highly potent platelet aggregation inhibitors at plasma levels as low as 1 pmol/ml. A preferred fibrinogen antagonist is the peptide cyclo(S,S)-N$^\alpha$-acetyl-Cys-(N$^\alpha$-methyl)Arg-Gly-Asp-Pen-NH$_2$ prepared by the method of Ali et al., published application EP 0 341 915 whose disclosure is herein incorporated by reference in its entirety. Also preferred is the peptide cyclo(S,S)-(2-mercapto)benzoyl-(N$^\alpha$-methyl)Arg-Gly-Asp-(2-mercapto)phenylamide which may be prepared by the method disclosed in published EPO 0423212, Application No. 90311537.6 whose disclosure is herein incorporated by reference in its entirety. The RGD peptides can generally be included into the microemulsion in an amount up to about 50 mg/ml of the aqueous phase.

Other fibrinogen antagonists useful in the present invention are those peptides disclosed in Pierschbacher et al., WO 89/05150 (US/88/04403); Marguerie, EP 0 275 748; Adams et al., U.S. Pat. No. 4,857,508; Zimmerman et al., U.S. Pat. No. 4,683,291; Nutt et al., EP 0 410 537; Nutt et al., EP 0 410 539; Nutt et al, EP 0 410 540; Nutt et al., EP 0 410 541; Nutt et al., EP 0 410 767; Nutt et al., EP 0 410 833; Nutt et al., EP 0 422 937; Nutt et al., EP 0 422 938; Alig et al., EP 0 372 486 Ohba et al., WO 90/02751 (PCT/JP89/00926); Klein et al., U.S. Pat. No. 4,952,562; Scarborough et al., WO 90/15620 (PCT/US90/03417); Ali et al., PCT US 90/06514, filed Nov. 2, 1990; peptide like compounds as disclosed in Alig et al., EP 0 381 033; and Alig et al., EP 0 384 362; and the cyclic RGD peptides:

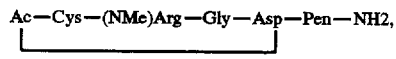

or

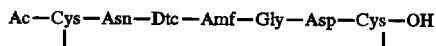

Dtc = 4,4'Dimethylthiazolidine-5-carboxylic acid
Amf = para-aminomethylphenylalanine Larger peptides/polypeptide also useful in the present invention are those disclosed in Pierschbacher et al., U.S. Pat. No. 4,589,881 (>30 residues); Bittle et al., U.S. Pat. No. 4,544,500 (20–30 residues); and Dimarchi et al., EP 0 204 480 (>34 residues).

Also preferred are growth hormone releasing peptides, which are peptides generally of twelve amino acids or less and effect the release of growth hormone. The growth hormone releasing peptides can be used in an amount up to about 75 mg/ml of the aqueous phase.

Exemplary of the class of growth hormone releasing peptides is the peptide His-D-TrP-Ala-TrP-D-Phe-Lys-NH$_2$ and other peptides which cause the release of growth hormone by essentially the same mechanism as His-D-Trp-Ala-Trp-D-Phe-Lys-NH$_2$. Another preferred growth peptide is Ala-His-D-Nal-Ala-Trp-D-Phe -Lys-NH$_2$. Growth hormone releasing peptides are disclosed, for instance, in Momany, U.S. Pat. No. 4,411,890; Momany, U.S. Pat. No. 4,410,513; Momany, U.S. Pat. No. 4,410,512; Momany, U.S. Pat. No. 4,228,158; Momany, U.S. Pat. No. 4,228,157; Momany U.S. Pat. No. 4,228,156; Momany, U.S. Pat. No. 4,228,155; Momany, U.S. Pat. No. 4,226,857; Momany U.S. Pat. No. 4,224,316, Momany U.S. Pat. No. 4,223,021; Momany, U.S. Pat. No. 4,223,020.; Momany, U.S. Pat. No. 4,223,019; Bowers et al., U.S. Pat. No. 4,880,778; Bowers et at., U.S. Pat. No. 4,880,777; Bowers et al., U.S. Pat. No. 4,839,344; Bowers et al., U.S. Pat. No. WO 89/10933 (PCT/US89/01829); Bowers et al., EP-A 398 961, Bowers et al. EP-A 400 051, all of which are fully incorporated herein by reference.

The present invention is particularly useful in methods of treatment for various medical indications which methods comprise administering an effective amount of the selected active agent as defined herein to a patient in need thereof. The disease states and uses of each of the active agents set forth herein is well known to those of skill in the art. The amount of the active agent required for therapeutic systemic administration will, of course, vary with the patient receiving the active agent, the active agent itself, and the nature and severity of the patient's condition.

The pharmaceutically-active compounds employed in the present invention also include immunogens which can be incorporated into vaccine adjuvant systems. The immunogens which are acceptable include purified proteins and peptides and derivatives thereof, and generally immunogens which have a weight average particle size in the range up to about 150 nm which therefore are capable of being maintained in the aqueous phase of the microemulsion.

The biologically active material is said to be a "water-soluble" material. Those skilled in the art will readily understand by the list of representative active materials that they are soluble to an effective extent in an aqueous phase and have negligible solubility in an organic phase. The solubility of the active materials in the aqueous phase at about 20° C. is at least about 1 part per 100,000 parts and preferably at least about 1 part per 10,000 parts. To achieve this level of solubility the pH or ionic strength of the aqueous phase may be altered. The solubility of the active materials in organic materials, such as those stated comprising the organic phase of the microemulsion, at about 20° C. is less than about 10 parts per 1,000,000 parts and preferably less than about 1 part per 1,000,000 parts. The water:oil partition coefficient is greater than 10:1, advantageously at least about 50:1, preferably at least about 100:1, and most preferably greater than about 1000:1. The water:oil partition coefficient is a commonly used quantity and refers to the ratio of the solubility of the material in water at about 20° C. to the solubility of the material in a reference oil, generally olive oil which is a mixture of triglycerides of saturated and unsaturated fatty acids esterified to glycerol, at about 20° C. The partition coefficient is determined by dissolving the active agent in an equal volume of water and olive oil (absent surfactant) and determining the solubility in each phase. As used herein, the reference oil is a U.S.P./N.F. grade olive oil available from various chemical suppliers including Spectrum Chemicals Mfg. Corp., Gardena, Calif.

The amount of active ingredient included in the internal aqueous phase may be varied considerably, depending upon its solubility and activity, the use for which it is intended, the amount of emulsion to be employed, and the like. Generally, as stated above, active ingredients in the amounts of $10^{-9}$ to 100% by weight/volume %, based on the volume of the internal aqueous phase, provide a satisfactory formulation for most applications. The biologically active material is preferably soluble in the w/o microemulsion; however in some cases it will be soluble upon the conversion to the o/w emulsion upon the addition of water to the system. The amount of active material to be administered to be "therapeutic" will be easily determined by those skilled in the art based upon concentration of dosage and the repetition of the dosage.

The w/o microemulsions may be formulated with agents for enhancing mucosal absorption of peptides and proteins. These include bile salts such as trihydroxy bile salts, i.e. cholate, taurocholate, and glycocholate, dihydroxy bile salts, i.e. deoxycholate, taurodeoxycholate, chenodeoxycholate, and ursodeoxycholate, triketo bile salts such as dehydrocholate. Non-ionic surfactants such as polyoxyethylene ethers with alkyl chain lengths from 12–18 carbon atoms and polyoxyethylene (POE) chain lengths from 2–60, p-t-octylphenoxypolyoxyethylenes with 2–60 POE groups, non-ylphenoxypolyoxyethylenes with 2–60 POE groups, polyoxyethylene sorbitan esters with 8–24 alkyl chain lengths and 4–80 POE groups, and 1-dodecylhexahydro-2H-azepin-2-one(azone, laurocapram) can be used. Anionic surfactants such as sodium dodecyl sulfate and dioctyl sodium sulfosuccinate can be used. Lysolecithins containing saturated fatty acyl chains having 8–24 carbon atoms or unsaturated fatty acyl chains having 1 to 4 double bonds and 16–24 carbon atoms can be used. Mono/diesters of glycerol, such as medium chain fatty acid mono/di-esters containing saturated fatty acids with 8–12 carbon atoms, and mono/di-glycerol esters of unsaturated fatty acids having 1 to 4 double bonds and 16–24 carbon atoms can be used. Acylcarnitines, acylcholines and acylamino acids can be used, such as acylcarnitines having 12–20 carbon acyl groups and where the acyl groups have 0–4 double bonds, acylcholines such as acyl choline esters of fatty acids having 8–22 carbon atoms and 0–4 double bonds, and acylamino acids such as Nacyl amino acids and dipeptides having acyl groups with 8–24 carbon atoms and 0–4 double bonds and the amino acids having $\alpha$ or $\beta$ amino groups and a molecular Weight less than 350. Additionally, mono and polyunsaturated fatty acids and their salts having 14–24 carbon atoms and 1–4 double bonds, and salicylic acid and its sodium salt, sodium 5-methoxysalicylate can be used.

The w/o microemulsions of this invention may readily be prepared by simply mixing together with mild agitation the selected components in the desired ratios at room temperature or at slightly elevated temperatures. As pointed out above, no high-energy mixing or application of heat is necessary, although limited use of each may be employed, if desired, to increase the rate of formation of the microemulsion. Moreover, the ingredients do not have to be added in any particular order other than that the active material be present in the aqueous phase as the emulsion is formed. Preferably, however, the surfactant should first be mixed with the oil phase, followed by the addition of water in the proper ratio. It is preferred to dissolve the active material in the water first, and then add this aqueous phase to the oil and surfactant components.

The size of the droplets, i.e., the number average diameter, in the resulting w/o microemulsion is usually 10–150 nanometers (nm), usually below 50–100 nm, with the majority of droplets below 100 nm, more preferably below 75. The particle size measurement is usually determined by laser light scattering techniques. The water-in-oil microemulsions are also characterized by their stable, clear homogeneous appearance.

The amount of water or aqueous fluid, e.g. aqueous body fluid, necessary to convert the w/o emulsion to an o/w emulsion when used, for example, for storing proteins, is not critical and may be determined routinely by titration of the microemulsion with excess water. Generally, however, it has been found that water in excess of about 1 to about 35 times that of the volume of the emulsion is sufficient for this purpose.

Besides the volume of water added or provided by the body itself, other factors which control the rate of release of any given drug include pH, temperature, and degree of agitation. Those skilled in the art will recognize that by varying these conditions in a generally known manner, the release of the drug can be slowed or increased as desired.

The microemulsion system of the present invention can be formulated with a high melting oil, that is, an oil with a melting point above room temperature (22°–23° C.), preferably above about 30° C., in order to formulate a microemulsion which is a solid at room temperature. Also, high melting surfactants such as a $C_{10-40}$ ester of a long chain fatty acid and alcohols having at least about 12 carbon atoms, wherein these surfactants have melting points above room temperature, preferably above about 30° C. Preferably, the microemulsion will melt at body temperatures, generally between about 35°–40° C. The amount of high melting oil and the melting point of that oil can vary, but the final composition containing the microemulsion is solid at room temperatures. The solid microemulsion system can be used as a suppository transport vehicle or as an oral transport vehicle. The oral formulation is preferably in tablet or capsule form. The microemulsion can either be formulated directly with the high melting oil, or the microemulsion can be formulated first, after which the high melting oil is blended with the microemulsion. Such high melting oils are well known in the art and include, for example, partially hydrogenated coconut oils, palm oils, cocobutter, hydrogenated peanut oil, and various hydrogenated vegetable oils, along with combinations thereof. Preferred oils include hydrogenated coconut and palm oils and mixtures thereof.

The w/o microemulsion system that is solid at room temperature (22°–23° C.) can be prepared using the high melting oil directly with the other components during formulation. The solution of components is heated to a slightly elevated temperature of from about 25°–60° C., preferably about 30°–50° C., during mixing and cooled to a solid at room temperature. The final w/o microemulsion system has component ranges within those previously stated for the liquid microemulsion systems. Preferred solid systems have from about 20–90%, preferably 30–70% w/w of a high melting oil having a melting point from about 85°–120° F.; from about 1–50%, preferably 3–20% w/w of the aqueous phase, and 5–80%, preferably 15–60% w/w of a surfactant or surfactant mixture having an HLB range as set forth in this invention. Preferably, the surfactant is a mixture of surfactants containing 2–30%, preferably 5–20% w/w (of the microemulsion) of the high HLB surfactant, and 4–50%, preferably 10–40% w/w (of the microemulsion) of the low HLB surfactant.

The w/o microemulsion system that is solid at room temperature can also be prepared by first preparing the w/o microemulsion without the high melting oil and dispersing this microemulsion in the high melting oil. First, the w/o microemulsion is prepared according to the present invention. Then, the high melting oil is blended with the w/o microemulsion. Commonly this is accomplished at slightly elevated temperatures between about 25°–60° C., preferably about 30°–50° C. The microemulsion is thereby dispersed within a matrix made of the high melting oil. The amount of high melting oil to microemulsion ranges from about 0.5:1 to about 2:1. This amount can vary beyond these ranges so long as a final dispersed microemulsion system is produced which is a solid at room temperature. The high melting oil is typically admixed with the low HLB surfactant prior to addition to the microemulsion in order to properly retain and disperse the microemulsion in the high melting oil.

It has been surprisingly found that by taking a certain w/o microemulsion system of the present invention, and adjusting it to have a higher effective HLB value, that the w/o microemulsion converts, upon addition of water, not just to an o/w emulsion as do all of the claimed w/o microemulsions, but rather to an o/w microemulsion. The higher HLB value is obtained in the present systems by the addition of a modifier which allows the w/o microemulsion HLB level to be increased beyond its normal stability level without the breaking of the w/o microemulsion. The final HLB level of the surfactant or surfactant mixture of these w/o microemulsions is greater than about 7, and is preferably from about 7 to about 16, most preferably from about 8–13. Modifiers found to be useful are incorporated into the aqueous phase of the microemulsion and include sorbitol, polyethylene glycol (PEG), mannitol, propylene glycol, mono- and disaccharides, and mixtures thereof. If proteins or peptides are incorporated into the aqueous phase, then preferred modifiers are mannitol, sorbitol, PEG, and mixtures thereof.

The more modifier added to the w/o microemulsion, the higher the HLB can be raised in the system with the retention of a w/o microemulsion. This higher HLB level allows for conversion to an o/w microemulsion. The precise amount of modifier and the precise amount of higher level HLB surfactant added to the w/o microemulsion is functionally determined by the presence of two end results: (1) the retention of the w/o microemulsion and (2) the conversion to an o/w microemulsion upon addition of water.

The amount of modifier added to the aqueous phase of the w/o microemulsion depends on the desired final HLB. Typically, a 10–95%, preferably a 20–70%, most preferably a 20–50% by weight aqueous modifier solution, preferably a sorbitol solution, can be employed as the modified aqueous phase for the w/o microemulsion. This sorbitol solution can contain physiological buffers and saline or other salts.

The particle size of the w/o microemulsion which converts to an o/w microemulsion is the same as afore-stated for the w/o microemulsions. The number average particle size of the converted o/w microemulsion is typically below about 100 nm, preferably between 10–100 nm, most preferably between 20–60 nm as determined by laser light scattering technique. The amount of water required to convert the w/o system to the o/w microemulsion can vary depending upon the composition of the w/o microemulsion. Typically the amount of water required ranges from about 1 to 10 times the volume of the w/o system. Larger amounts of water can be used to convert the w/o systems, and amounts up to 1000 times the volume of the w/o system, preferably about 3 to about 100 times the volume of the w/o system are used to convert to the o/w microemulsion.

These w/o converting to o/w microemulsion systems can be advantageously employed as transport vehicles for water soluble drugs which degrade in the oil phase, such as certain peptides, proteins, and immunogens used for oral or suppository formulations. Also, these formulations are preferred for intravenous and intraarterial administration. The risk of emboli formation is greatly reduced due to the exceedingly small particle sizes produced upon conversion with excess bodily fluid.

These w/o converting to o/w microemulsion formulations can also be used as nutritional lipid emulsions, and especially as total parenteral nutrition formulations. The w/o system can be converted using an aqueous phase containing water soluble nutrients to form lipid-in-water microemulsions just prior to administration.

The w/o microemulsions containing the biologically active material in the aqueous phase of the present invention are preferably administered parenterally, enterally and via other mucous membranes such as nasally, rectally, vaginally, or via the colon. After administration, the biological effect upon the animal caused by the active material can be measured or observed. The convertible microemulsion system enhances both the drug activation and uptake at the site of conversion. The unique convertibility feature of the present microemulsions provides that the drug will be maintained primarily in the aqueous phase due to oil phase insolubility. This is advantageous in that certain active materials may become inactivated if dispersed within an oil phase or if dissolved within an aqueous phase outside of an emulsion. Generally, such active materials as proteins and peptides employed in the present invention display a greater activity level when stored in the o/w microemulsion system as compared to their being stored for the same period of time and under the same conditions in the same aqueous phase that is not contained within an emulsion system.

The oral administration of a biologically active material, contained within the w/o microemulsion drug delivery system of the present invention, can be in the form of a capsule or tablet. The capsule is generally a starch or gelatin material. Certain active materials may be susceptible to the low pH environment of the stomach and should therefore be delivered to the higher pH environment of the intestinal system. Although such active materials are beneficially delivered in suppository form, if oral delivery is desired, the capsule or tablet can be supplied with an enteric coating. Such coatings are well known in the art as are the methods of enterically coating a capsule or tablet. The method of producing an enterically coated capsule using the w/o microemulsion system of the present invention is as follows. The w/o microemulsion containing the active agent is prepared and this composition is then placed into a capsule. The capsule is then coated with an enteric coating solution. The enteric coating solution contains the polymeric enteric coating substance and solvents. The polymeric enteric coating substance is generally a pharmaceutically acceptable polymer that will dissolve upon contact with intestinal fluids, pH of about 5.5 to 7.0, but will not dissolve in the lower pH stomach fluids. Enteric polymer coatings are readily available commercially, such as the Eastman® C-A-P™ (cellulose acetate phthalate) and C-A-T (cellulose acetate trimellitate) enteric coating materials available from Eastman Chemical Products, Inc. Various techniques are known to apply the entire polymer coating such as spray coating or immersion coating and several layers of the enteric substance may be required.

As aforestated, in yet another embodiment, our microemulsions may be used to prepare non-drying topical, as opposed to transdermal, salves and ointments. These may readily be prepared by simply admixing a therapeutically-active amount of the emulsion with known topical petroleum bases or the like customarily employed for skin application, as long as these materials are compatible with the emulsion. The w/o microemulsion is ideally suited for wound care treatment where the dry epidermal skin layer, the stratum corneum or horny layer, is removed thereby exposing the aqueous-based dermal skin layer, as for example in burn wounds. The w/o microemulsion can also be used where the dermal skin layer is also partially removed. The w/o microemulsion, when contacted with the dermal or lower body layer converts to an o/w emulsion upon the addition of aqueous bodily fluids. Preferably, proteases, such as serine, metallo, cysteine, aspartyl, and the like which degrade connective tissue proteins such as collagen and elastin and the like, along with growth factors are used as the active material to aid in the removal and repair of skin tissue. Examples of growth factors include, for example, platelet derived growth factor, PDGF, epidermal growth factor, EGF, transforming growth factors, TGFα and TGFβ, and insulin-like growth factor, IGF-I and IGF-II, and the like. These active materials generally have average particle sizes of greater than 1 to about 100, preferably from about 3 to about 30, nanometers. Typically, the molecular weight of these active materials is at least about 5000 and up to over 40,000, preferably from about 5,000 to about 35,000. The average human epidermis pore size is below about 1 nm, and therefore the active materials employed in the topical systems do not effectively traverse the epidermis skin layer.

The topical microemulsion system acts as a reservoir for providing a stable protein to the wound site. The topical microemulsion is preferably presented in the form of a solid, salve, or gel that can be easily removed from the wound site by washing with aqueous fluid. Most preferably, the topical is presented as a solid or semi-solid (deforming upon application of pressure) to maintain the w/o microemulsion at the wound site for conversion and release of the drug.

A further embodiment of the present invention encompasses the use of the w/o microemulsion as a carrier system to be used in a vaccine adjuvant system. In such a vaccine adjuvant system, the immunogen is admixed into the aqueous phase. This aqueous phase is then admixed with the oil phase which contains the surfactant. These adjuvant systems can also be formulated with an immuno-stimulator which are well-known in the vaccine adjuvant art. Such immuno-stimulators include Such compounds as muramyl di- or tri-peptide and derivatives thereof; interferons, and interleukins. The aqueous phase may also contain inorganic salts, buffering agents, preservatives, and the like, in addition to the immunogen.

The microemulsion vaccine adjuvant system of the present invention is characterized by its stability and long shelf life, in comparison to emulsion adjuvant systems of the prior art. The use of the oils of the present invention, which are referred to as biodegradable oils, to formulate the microemulsion system provides benefits over previous emulsion adjuvant systems in that the production of granulomas is believed to be decreased. The w/o microemulsion adjuvants can readily convert to oil-in-water emulsions when administered into the body which allows for the generation of macrophage stimulating oil droplets in situ. The smaller and more uniform size of the resulting droplets also is expected to lead to a more reproducible response to a given immunogen.

The w/o microemulsion systems of the present invention can also be prepared in the absence of the active material. Such systems have various uses, but are primarily useful as pharmaceutical compositions into which an active agent, such as those defined in this invention, can be incorporated.

The invention will now be illustrated by, but is not intended to be limited to, the following examples.

EXAMPLES

Formulation and Convertibility

Several formulations of the water-in-oil (w/o) microemulsions of this invention were prepared in which, by way of illustration, the components, and their ratios, provide convertible microemulsions. For convenience, a drug was not included in every instance, but it will be understood that any water-soluble drug, as defined above can be added into the microemulsion.

In preparing each formulation, the following general procedure was employed:

Into a small vial was pipetted a measured amount of oil, followed by the addition of a surfactant, or mixture of surfactants, of a given HLB value. The vial was then shaken with a vortex mixer for a given number of minutes until the surfactant and oil were evenly mixed. A saline solution was then added to the oil/surfactant mixture and the mixture shaken a few minutes until an optically clear w/o emulsion was recovered. Its stability is measured by periodic visual inspection for the presence of macroscopic phase separation, as shown by cloudiness or the formation of two distinct layers. Stable means the emulsion is clear and single phase.

The physical characteristics of the microemulsions can be tested including such properties as viscosity, conductance and refractive indices.

Example 1

Water-in-oil microemulsion compositions were prepared having the following components:

TABLE 1

| Composition | Captex 200 | Captex 800 | Imwitor 308 | Glycerol Monocaprate | Tween 80 | Aqueous |
|---|---|---|---|---|---|---|
| A | 59.4 | | 15.3 | | 15.3 | 10 |
| B | 59.8 | | | 15.4 | 15.4 | 9.4 |
| C | | 50 | 36 | | 8 | 6 |

Captex 200 - Propylene glycol dicaprylate/caprate having a fatty acid composition of caproic (4.1), caprylic (68.29), capric (27.4%), lauric and higher (0.2), manufactured by Karlshamns Lipid Specialties USA.

TABLE 1-continued

| Compo-sition | Captex 200 | Captex 800 | Imwitor 308 | Glycerol Monocaprate | Tween 80 | Aqueous |
|---|---|---|---|---|---|---|

Captex 800 - Propylene glycol dioctanoate, manufactured by Karlshamns Lipid Specialties USA.
Imwitor 308 - Glycerol caprylate (80–90% $C_{11}$ monoglyceride), manufactured by Huls America, Inc.
Glycerol Monocaprate - 1-monodecanoyl-rac-glycerol (99% $C_{13}$ monoglyceride), manufactured by Sigma Chemical.
Tween 80 - polyoxyethylene sorbitan mono oleate, HLB = 15, manufactured by Sigma Chemical.

Example 2

The effectiveness of the w/o microemulsions of the present invention were demonstrated by a calcein bioavailability and uptake study. The experiment was conducted by employing the standard unconscious rat model of Walker et al., Life Sciences, 47, 29–36, 1990, using the model compound calcein, 5(6)-carboxyfluorescein. The calcein is a fluorescent compound and therefore its presence in the blood system can be readily detected using fluorescence spectroscopy. The w/o microemulsions were dosed via i.d. at 3.0 µmol/kg (1.0 ml/kg microemulsion). The microemulsions of Example 1 were used in the study and compared to dosing of calcein in a saline solution. The results of the calcein study are shown in Table 2.

TABLE 2

| Microemulsion Composition | Calcein Bioavailability (%) |
|---|---|
| A | 22 |
| B | 22.2 ± 6.1 |
| C | 22.9 ± 5.3 |
| Saline | 1.3 ± 0.5 |

Example 3

Phase diagrams were prepared according to the present invention. All phase diagrams are in weight percents.

A phase diagram was prepared to depict the various microemulsion formulations existing using an oil phase consisting of Captex 200, Imwitor 308 as the low HLB surfactant, Tween 80 as the high HLB surfactant, and saline as the aqueous phase. The phase diagram is shown in FIG. 1.

Figure 2:
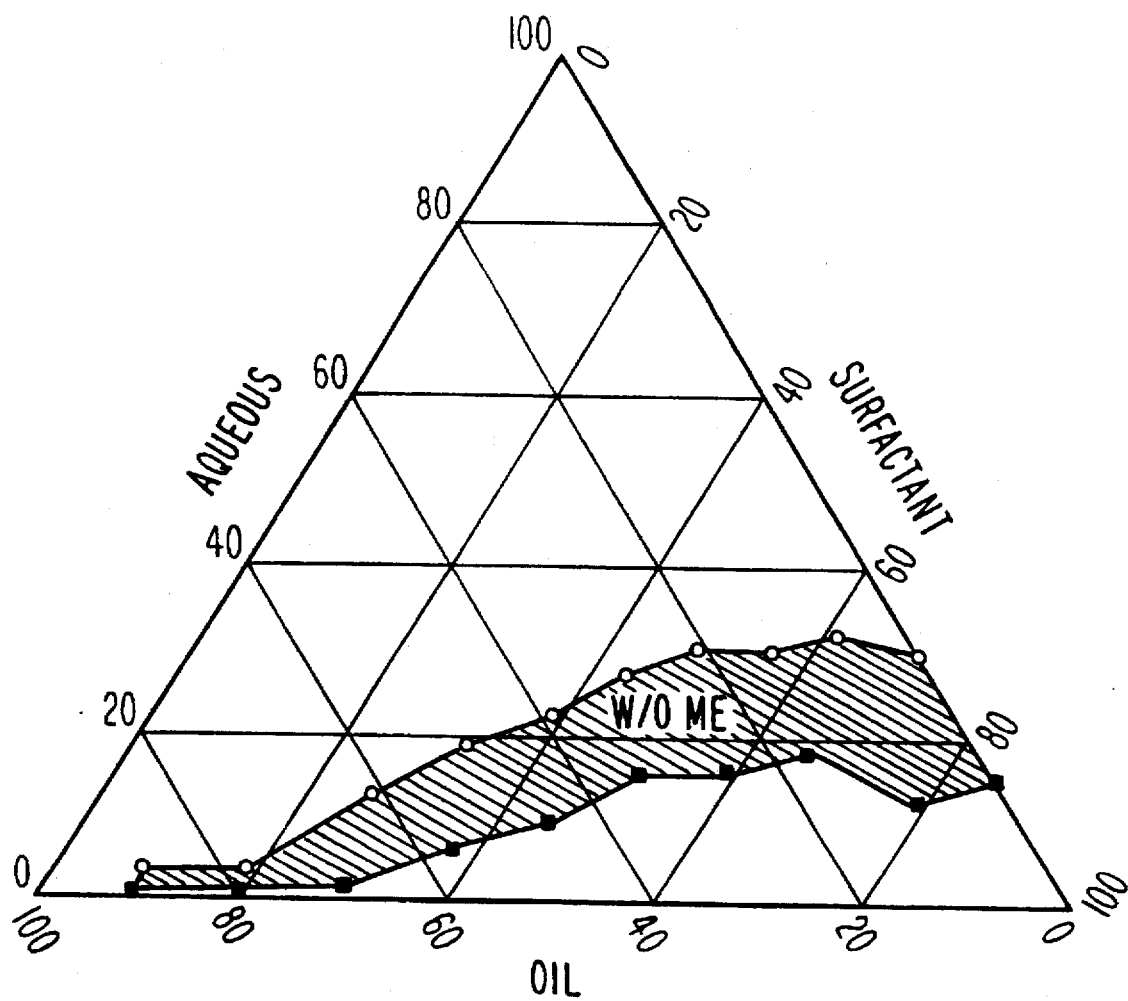
FIG. 2 is a phase diagram depicting the various microemulsion formulations existing using an oil phase consisting of Caprex 8000, Imwitor 308 as the low HLB surfactant, Tween 80 as the high HLB surfactant, and saline as the aqueous phase.

A phase diagram was prepared to depict the various microemulsion formulations existing using an oil phase consisting of Captex 8000 (tricaprylin, Karlshamns), Imwitor 308 as the low HLB surfactant, Tween 80 as the high HLB surfactant, and saline as the aqueous phase. The phase diagram is shown in FIG. 2.

Figure 3:
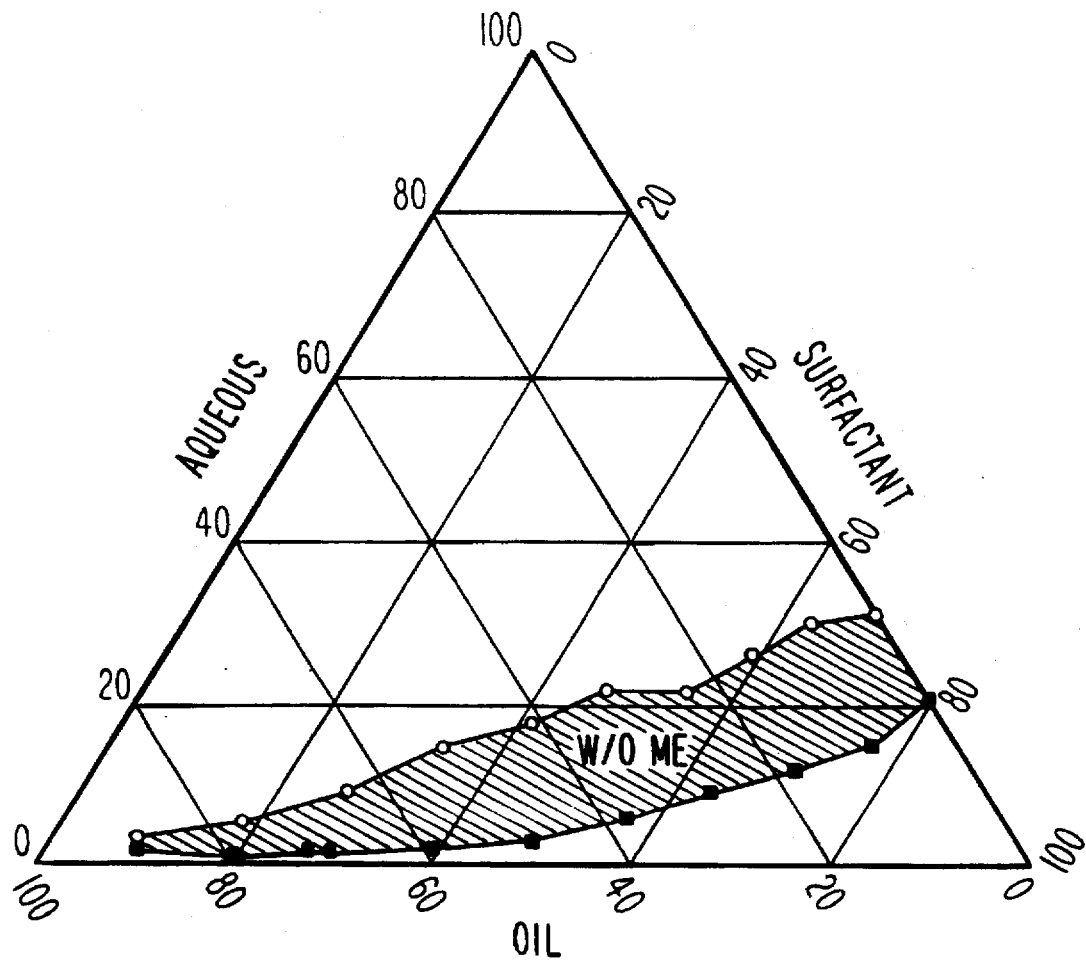
FIG. 3 is a phase diagram depicting the various microemulsion formulations existing using an oil phase consisting of Caprex 200, Imwitor 308 as the low HLB surfactant, Glucamate SSE-20 as the high HLB surfactant, and saline as the aqueous phase.

A phase diagram was prepared to depict the various microemulsion formulations existing using an oil phase consisting of Caprex 200, Imwitor 308 as the low HLB surfactant, Glucamate SSE-20 (PEG-20 methyl glucose sesquistearate, HLB 12.5, Amerchol Corp.) as the high HLB surfactant, and saline as the aqueous phase. The phase diagram is shown in FIG. 3.

Figure 4:
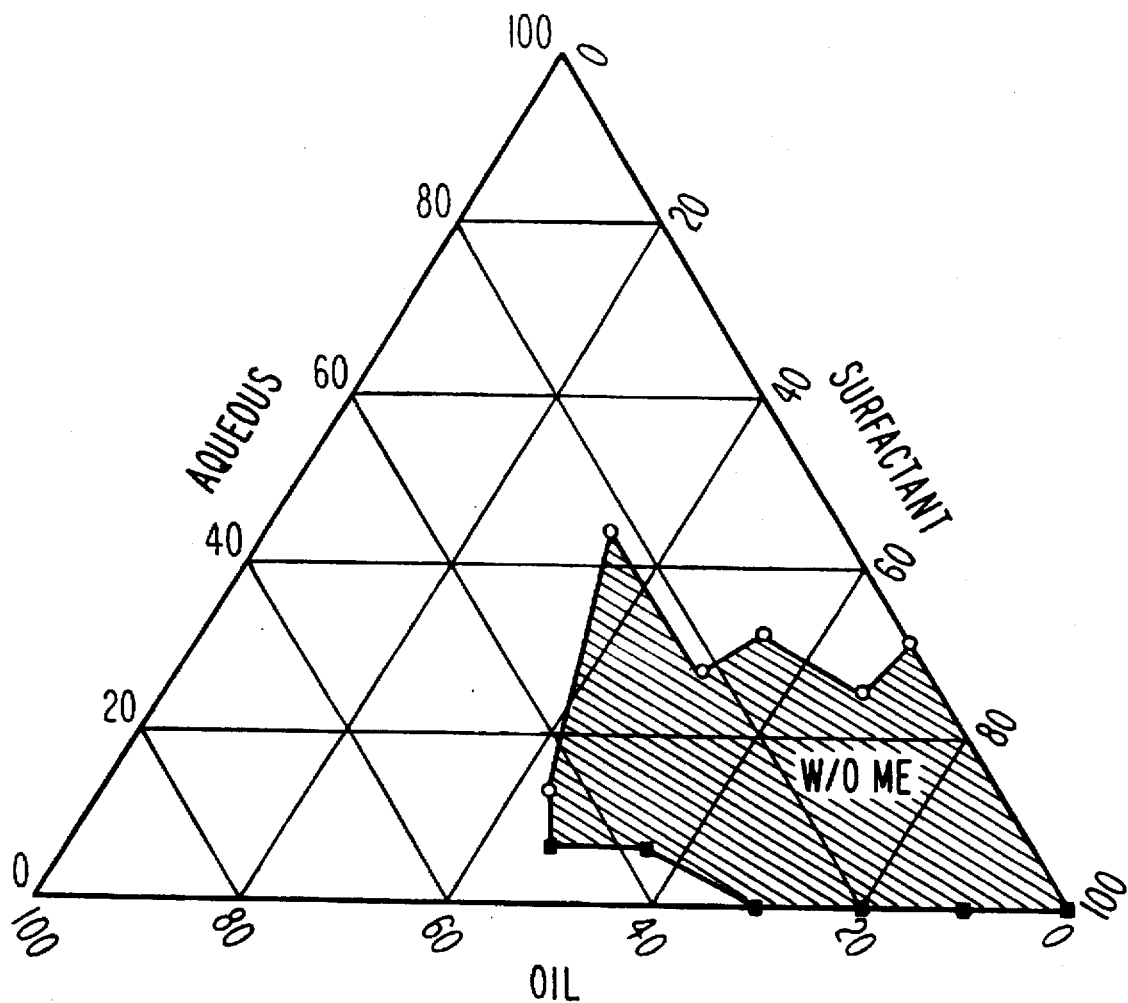
FIG. 4 is a phase diagram depicting the various microemulsion formulations existingusing an oil phase consisting of Caprex 200, Imwitor 308 as the low HLB surfactant, Brij 30 as the high HLB surfactant, and saline as the aqueous phase.

A phase diagram was prepared to depict the various microemulsion formulations existing using an oil phase consisting of Captex 200, Imwitor 308 as the low HLB surfactant, Brij 30 (polyoxyethylene 4 lauryl ether, HLB 9.7, ICI America) as the high HLB surfactant, and saline as the aqueous phase. The phase diagram is shown in FIG. 4.

Figure 5:
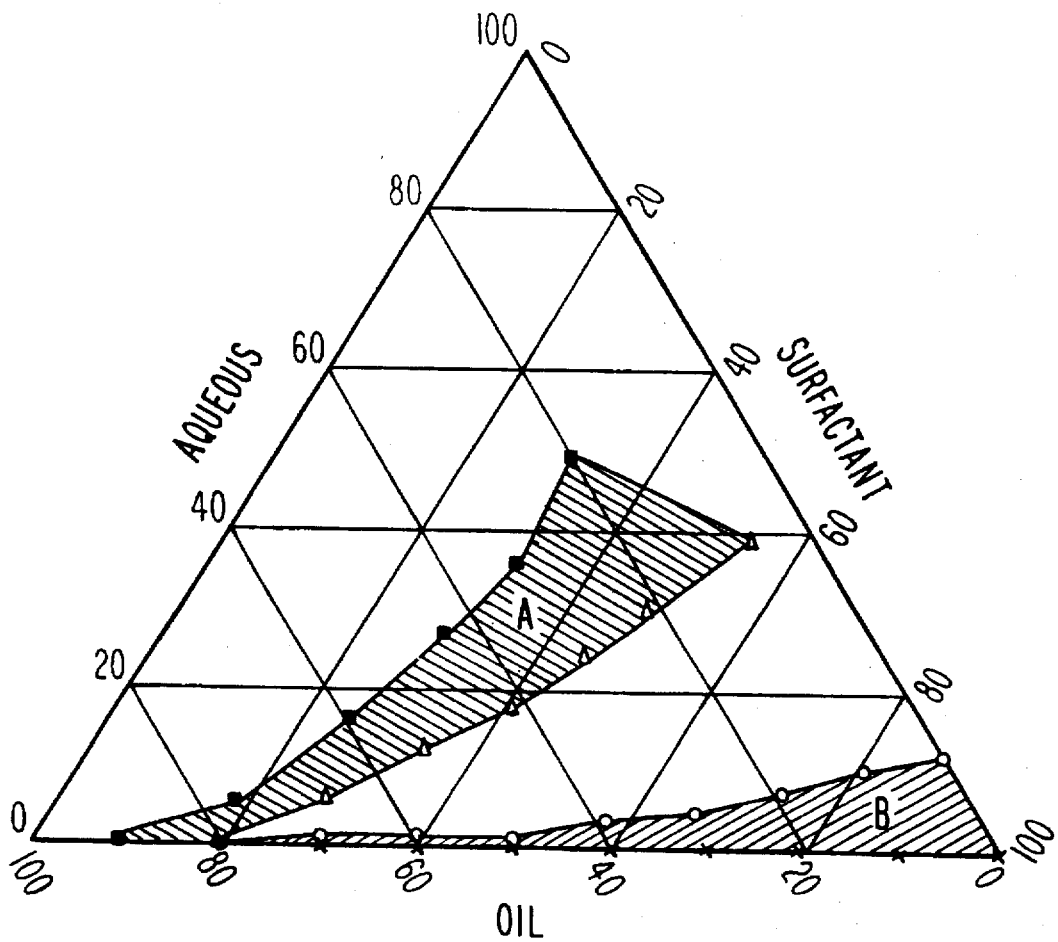
FIG. 5 is a phase diagram depicting the various microemulsion formulations that are solids at about 23° C. using an oil phase consisting of Witepsol H-15 and Captex 800, Imwitor 308 as the low HLB surfactant, Tween 80 as the high HLB surfactant, and saline as the aqueous phase.

A phase diagram was prepared to depict the various microemulsion formulations that are solids at about 23° C. using an oil phase consisting of Witepsol H-15 (a 90:10 mixture of triesters:diesters of glycerol and lauric acid, m.p. 33°–36° C., Huls America) and Captex 800 (propylene glcol dioctanoate, Karlshamns), Imwitor 308 as the low HLB surfactant, Tween 80 as the high HLB surfactant, and saline as the aqueous phase. The phase diagram is shown in FIG. 5.

Example 4

The bioavailability of calcitonin (used in the treatment of hypercalcemia by lowering $Ca^{+2}$ serum levels) was determined using an unconscious rat model. The microemulsion formulation contained 45 wt. % Captex 200, 25 wt. % Imwitor 308, 15 wt. % Tween 80, 10 wt. % lauroyl choline, and 5 wt. % buffer solution containing salmon calcitonin (20 mM acetate buffer solution containing 680 i.u. calcitonin/ml; pH 4.5). The formulation was prepared by heating the surfactants to 50° C., admixing the Captex 200, and then cooling to about 37° C. and admixing the aqueous phase.

Five fasted rats (male Sprague-Dawley) were anaesthetized with i.p. pentobarbital. An incision in the neck was made to reveal the jugular vein. A catheter was inserted into the jugular vein to collect blood samples for calcium analysis. An incision was made into the peritoneal cavity and the duodenum was exposed. A purse-string suture was introduced into the surface of the duodenum.

The juvenile male rats in this study weighed between 90 and 160 grams. The animals were dosed with 0.5 mL of microemulsion per kilogram body weight. The 0.5 mL dosage of microemulsion contained 17 i.u. of salmon calcitonin.

After the microemulsion was introduced, the purse-string suture was tightened as the syringe needle was withdrawn to prevent leakage of the microemulsion into the peritoneal cavity.

The peritoneum was closed with surgical staples and the animals were kept anaesthetized through the duration of the experiment. Blood samples (50 to 10 µl) were taken periodically during the course of the three hour experiment. The blood samples were used to prepare serum which was used to determine serum $Ca^{+2}$ (free ionized calcium) levels using Beckman 700 calcium clinical assay kits. The serum calcium levels are reported in Table 4.1 are in units of mg/dL.

TABLE 4.1

| | Calcium Assay Results | |
|---|---|---|
| Time | Serum Calcium Levels | ±SEM (N = 5) |
| −15 min | 6.8 | 0.42 |
| 15 min. | 7.5 | 0.54 |
| 45 min. | 5.0 | 0.19 |
| 135 min. | 6.2 | 0.52 |
| 165 min. | 6.2 | 0.56 |

Calcium levels dropped significantly 45 minutes after i.d. dosing with the microemulsion and remained lower than pre-dose values for at least 165 minutes.

Example 5

Microemulsion formulations containing 1.2 mg/mL Growth Hormone Releasing Peptide (His-D-Trp-Ala-Trp-D-Phe-Lys-$NH_2$; Momany—U.S. Pat. No. 4,411,890) were delivered rectally at 1 mL/Kg (animal weight) to evaluate the bioavailability in a rat model.

The microemulsion formulation contained 60% wt. Captex 200, 15% wt. Imwitor 308, 15% wt. Tween 80, and 10% wt. saline containing the peptide.

The juvenile, male Sprague-Dawley rats weighing between 262–343 g were fasted 18 hours prior to dosing and were divided into two treatment groups. The animals were anesthetized with Pentobarbital (Nembutal) at 60 mg/Kg body weight. Test group animals were dosed rectally with 1 mL microemulsion/Kg animal at a 1.2 mg GHRP/mL concentration. The control group was dosed rectally with 1 mL/Kg of buffer containing 1.2 mg/mL GHRP. Jugular catherization was used to collect blood samples. A 0.3 mL baseline blood sample was taken prior to dosing. After dosing blood was drawn at the following time points 1, 5, 10, 15, 30, 45, 60, 90, and 120 mins. The rGH levels in the plasma were measured using an Amersham rGH [$^{125}$I] assay system at a 1 to 25 dilution. Any value greater than 30 ng/ml tube is considered a significant response.

The test group reached an average peak value of 132.39 ng/ml tube at 15 min and dropped to 23 ng/ml tube at 45 min. The buffer group reached an average peak value of 84 ng/ml tube at 15 min and dropped to 30.14 ng/ml tube at 60 min. The test results for the rGH levels in the plasma (ng/ml) are shown in Tables 5.1 and 5.2 for the microemulsion group and the control group, respectively.

TABLE 5.1

TEST GROUP USING MICROEMULSION

| TIME | ANI-MAL 1 | ANI-MAL 2 | ANI-MAL 3 | ANI-MAL 4 | ANI-MAL 5 | MEAN | SEM |
|---|---|---|---|---|---|---|---|
| 0 | 11.39 | 5.69 | 5.48 | | 5.51 | 7.02 | 1.45 |
| 1 | 19.89 | 9.16 | 7.32 | 4.19 | 4.89 | 9.09 | 2.848 |
| 5 | 106.93 | 54.41 | 45.43 | 33.56 | 26.68 | 53.40 | 14.20 |
| 10 | 214.68 | 87.94 | 124.33 | 74.07 | 62.23 | 112.45 | 27.64 |
| 15 | 167.03 | 104.00 | 194.25 | 93.61 | 103.06 | 132.39 | 20.24 |
| 30 | 60.08 | 34.98 | 78.28 | 86.05 | 75.75 | 67.03 | 9.05 |
| 45 | 15.80 | 13.30 | 34.60 | 28.76 | 22.78 | 23.05 | 3.95 |
| 60 | 9.87 | 7.48 | 24.27 | 7.30 | 9.82 | 11.75 | 3.17 |
| 90 | 6.95 | 6.90 | 30.35 | 7.07 | 3.61 | 10.97 | 4.88 |
| 120 | 8.52 | 14.66 | 6.23 | 3.98 | 8.02 | 8.28 | 1.78 |

TABLE 5.2

CONTROL GROUP USING BUFFER

| TIME | ANI-MAL 1 | ANI-MAL 2 | ANI-MAL 3 | ANI-MAL 4 | ANI-MAL 5 | MEAN | SEM |
|---|---|---|---|---|---|---|---|
| 0 | 23.64 | | 9.86 | 10.35 | 10.57 | 13.60 | 3.34 |
| 1 | 20.42 | 10.29 | 7.50 | 10.96 | 11.82 | 12.20 | 2.17 |
| 5 | 70.10 | 10.46 | 14.19 | 40.42 | 39.93 | 35.02 | 10.77 |
| 10 | 104.96 | 10.24 | 17.35 | 55.68 | 69.08 | 51.46 | 17.39 |
| 15 | 193.21 | 11.36 | 31.02 | 76.27 | 110.55 | 84.48 | 32.22 |
| 30 | 155.39 | 10.91 | 59.33 | 68.83 | 74.05 | 73.70 | 23.28 |
| 45 | 72.96 | 17.95 | 22.20 | 27.54 | 50.29 | 38.19 | 10.32 |
| 60 | 49.55 | 12.01 | 49.65 | 13.03 | 26.46 | 30.14 | 9.34 |
| 90 | 37.47 | 6.97 | 21.31 | 2.56 | 10.25 | 15.70 | 6.26 |
| 120 | 34.91 | <1 | 13.23 | 4.23 | 10.40 | 15.69 | 6.67 |

Example 6

Experiments can be carried out using rats with the w/o microemulsion of this invention to evaluate them as a vehicle for the delivery of RGD peptides, such as the peptide cyclo(S,S)-N$^{\alpha}$-acetyl-Cys-(N$^{\alpha}$-methyl) Arg-Gly-Asp -Pen-NH$_2$.

Formulations

The test microemulsion systems are prepared according to the methods of the application, such as those set forth in Example 3.

Test Method

Intravenous (i.v.) Administration: Fasted rats are anesthetized with an intraperitoneal (i.p.) injection and surgically fitted with a jugular catheter (ACUC protocol #90-151). Rats are allowed to recover from the surgery for 1 day. Catherized rats are fasted for 18 hr prior to the experiment. Each rat receives either a 1 mg or 3 mg peptide/kg animal dose by lateral tail-vein administration. Blood samples of 0.5 ml aliquots are collected at 0, 1, 3, 5, 10, 15, 30, 45, 60, 90, 120, 150, and 180 min. The 0 min sample is taken 15 min prior to administration of the dose. Plasma is removed from the whole blood by centrifugation at 1600 xg for 5 min, and then plasma is stored at −20° C. in 250 µl aliquots per sample. The blood pellet is reconstituted with 12.5 units heparinized saline and returned to the appropriate rat via the jugular catheter. After the experiment, rats are euthanized with i.v. administration of pentobarbital.

Intraduodenal (i.d.) Adminstration: Fasted rats are administered an i.p. injection of anesthesia cocktail and surgically fitted with jugular and duodenal catheters. Rats are allowed to recover from the surgery for 4–5 days (ACUC protocol #91-055). Catherized rats are fasted 18–20 hr prior to the experiment. Each group of rats receives either 10 mg peptide/kg animal in each microemulsion (3.3 ml/kg) or 6.5 mg peptide/kg animal in each microemulsion (3.3 ml/kg). A saline control is administered to a group of rats containing 10 mg peptide/kg animal in a saline solution. Blood samples of 0.5 ml aliquots are collected via jugular catheter in heparinized eppendorf tubes at 0, 10, 30, 60, 120, 180, 240, and 1440 min. The 0 min sample is taken 15 min prior to administration of the dose by duodenal catheter. Plasma is collected for analysis and the blood returned to rats as described in the i.v. administration protocol. After 24 hr, rats are euthanized by i.v. administration of pentobarbital, exsanguinated, and a macroscopic observation of the intestinal tract is performed.

Post-Column HPLC Fluorescence Assay: For samples and standards, plasma components are precipitated with 0.6 ml cetonitrile, and then pelleted by centrifugation at 16,000 xg for 20 min. The supernatant is removed, and then dried to powder under N$_2$ at 40° C. Powder is dissolved in 0.5 ml 1% TFA solution, and then processed by solid-phase extraction procedure (SPEP). SPEP is as follows: 1) condition 1 ml columns with methanol, and then rinse columns with 1 ml water, 2) standards and samples are applied to columns, and then rinsed twice with 1 ml water, 3) standards and samples are collected in tubes upon elution from column with methanol by two 0.5 ml aliquots. The samples and standards are dried to powder under N$_2$ at 40° C., and then dissolved in 100 µl of 10% methanol:90% ultrapure water solution. Standards and samples are placed in HPLC vials. Vials with standards are placed before and after vials containing the samples for HPLC analysis. For the peptide standards, an aliquot is injected for analysis based on the concentration of the standard as follows: 50 µl aliquot is injected for analysis by post-column fluorescence detection. Fluorescence chromatography data are collected and integrated using Nelson Chromatography Data System. The peak area ratio (Y) and peptide standard concentration (X) are used to determine the slope of a line which is forced through the origin from the equation: slope=(sum of X*Y)/(sum of $X^2$). The slope represents the relationship between peak area ratio and peptide plasma concentration for the samples.

Results

The area under the plasma concentration curve (AUC) is determined for each test group. The percentage bioavailability is determined by the equation with the average AUC from iv administration:

$$[(AUC_{i,d}/AUC_{i,v})*(mg/kg_{i,v}/mg/kg_{i,d})]*100.$$

Example 7

Studies were conducted to determine whether the microemulsions of the present invention could enhance the bioavailability of the proteinaceous material disclosed in U.S. Pat. No. 4,703,036 (N-methyl-D-phenylalanyl-n-proplyl-L-argininal sulfate), which is incorporated herein in its entirety, which is a tripeptide-aldehyde derivative having a molecular weight of about 515 (CAS No. 126721-07-1), the peptide having anticoagulant activity.

The microemulsion formulation contained 60% wt. Caprex 200, 15% wt. Imwitor 308, 15% wt. Tween 80, 9% wt. 20 mM acetate buffer, 0.7% wt. peptide, and 0.3% wt. 1N HCl. A control composition contained the peptide in saline. Both preparations contained 5 mg peptide/ml composition.

Male Fisher 344 rats were anesthetized with methoxyflurane, and a midline abdominal incision was made to expose the intestine and 5mg peptide/kg animal in the form of the microemulsion was injected into the duodenal lumen distally. The injection site and surgical incision site were closed with surgical adhesive and the animals were allowed to recover. Blood samples were collected in heparinized Vacutainer tubes via cardiac puncture at appropriate times. Blood was reduced to plasma and plasma samples were analyzed for the peptide by HPLC with UV detection.

The results, based upon 3 rats dosed with the microemulsion formulation and 3 rats dosed with the saline composition, showed an increased uptake by the microemulsion formulation. The calculated area under the curve (AUC) for the microemulsion was 2019 ng-hr/ml while the AUC for the saline was 534 ng-hr/ml. The calculated bioavailability of the peptide for the microemulsion was 40% and for the saline was only 10.5%.

---

What is claimed is:

1. A stable, water-in-oil microemulsion composition suitable for storage and administration of biologically active materials, comprising:
   (a) from about 5 to about 99 volume percent of an oil phase comprising at least one pharmaceutically acceptable oil;

(b) up to about 60 volume percent of an aqueous phase comprising water;

(c) a biologically active material having a water:oil partition coefficient greater than 10:1;

(d) from about 1 to about 70 volume percent of a mixture of surfactants having a combined HLB value of from about 7 to about 14 comprising (i) a low HLB surfactant having an HLB below 8, said low HLB surfactant being at least 80 percent by weight of a $C_9$ monoglyceride, $C_{10}$ monoglyceride, $C_{11}$ monoglyceride, $C_{12}$ monoglyceride, or $C_{13}$ monoglyceride, and (ii) at least one surfactant having an HLB value above about 8.

2. The water-in-oil microemulsion composition of claim 1 wherein the active material is a therapeutic and is a protein or a peptide.

3. The water-in-oil microemulsion composition of claim 2 wherein said water-in-oil microemUlsion composition contains a low HLB surfactant component that is at least 80 percent by weight of a surfactant selected from the group consisting of $C_9$ monoglycerides, $C_{10}$ monoglycerides, $C_{11}$ monoglycerides, $C_{12}$ monoglycerides, $C_{13}$ monoglycerides, or mixtures thereof.

4. The water-in-oil microemulsion composition of claim 3 wherein said low HLB surfactant component is at least 90 percent by weight of said monoglycerides.

5. The water-in-oil microemulsion composition of claim 3 Wherein said low HLB surfactant component is at least 95 percent by weight of said monoglycerides.

6. The water-in-oil microemulsion composition of claim 3 wherein the oil phase comprises $C_{9-45}$ triglycerides, $C_{7-55}$ diesters of propylene glycol, and mixtures thereof.

7. The water-in-oil microemulsion composition of claim 3 wherein said low HLB surfactant component contains at least 80 percent by weight of a $C_{11}$ monoglyceride.

8. The water-in-oil microemulsion composition of any of the claims 1, 2, 3, 4, 5, 6 or 7 wherein the composition is a solid at about 23° C.

9. The water-in-oil microemulsion composition of any of the claims 1, 2, 3, 4, 5, 6 or 7 wherein the composition is a liquid at about 23° C.

10. The water-in-oil microemulsion composition of any of the claims 2, 3, 4, 5, 6, or 7 wherein the biologically acitve material is selected from the group consisting of RGD peptides, calcitonins, insulins, fibrinogen antagonists, growth hormone releasing peptides, interleukins, erythropoietins, colony stimulating factors, hematoregulatory peptides, vasopressin, collagenase inhibitors, angiotensin inhibitors, mammalian growth hormones, heparins, clotting factors, tissue plasminogen activators, atrial natriuretic peptides, and tumor necrosis factor.

11. A stable, water-in-oil microemulsion composition suitable for storage and administration of biologically active materials, comprising:

(a) from about 5 to about 99 volume percent of an oil phase comprising at least one pharmaceutically acceptable oil;

(b) up to about 60 volume percent of an aqueous phase comprising water;

(c) a biologically active material that is a therapeutic and is a protein or peptide and has a water:oil partition coefficient greater than 10:1;

(d) from about 1 to about 70 volume percent of a mixture of surfactants having a combined HLB value of greater than about 7, comprising (i) a low HLB surfactant having an HLB below 8, said low HLB surfactant being at least 80 percent by weight of a $C_9$ monoglyceride, $C_{10}$ monoglyceride, $C_{11}$ monoglyceride, $C_{12}$ monoglyceride, or $C_{13}$ monoglyceride, and (ii) at least one surfactant having an HLB value above about 8, and (e) a modifier, present in an amount sufficient to cause the water-in-oil microemulsion to convert to an oil-in-water microemulsion upon the addition of aqueous fluid.

12. The water-in-oil microemulsion composition of claim 11 wherein the modifier comprises sorbitol, polyethylene glycol, propylene glycol, mannitol, disaccharides, or mixtures thereof.

13. The water-in-oil microemulsion composition of claim 2 wherein said water-in-oil microemulsion composition contains a low HLB surfactant component that is at least 80 percent by weight of a surfactant selected from the group consisting of $C_9$ monoglycerides, $C_{10}$ monoglycerides, $C_{11}$ monoglycerides, $C_{12}$ monoglycerides, $C_{13}$ monoglycerides, or mixtures thereof.

14. The water-in-oil microemulsion composition of any of the claims 11, 12, or 13, wherein the composition is a solid at about 23° C.

15. The water-in-oil microemulsion composition of any of the claims 11, 12, or 13 wherein the composition is a liquid at about 23° C.

16. A method of administering to animals a water-in-oil microemulsion composition, comprising:
   (a) providing a water-in-oil microemulsion comprising
      (1) from about 5 to about 99 volume percent of an oil phase comprising at least one pharmaceutically acceptable oil;
      (2) up to about 60 volume percent of an aqueous phase comprising water;
      (3) a biologically active material that is therpeutic and has a water:oil partition coefficient greater than 10:1;
      (4) from about 1 to about 70 volume percent of a mixture of surfactants having a combined HLB value of from about 7 to about 14 comprising
         (i) a low HLB surfactant having an HLB below 8, said low HLB surfactant being at least 80 percent by weight of a $C_9$ monoglyceride, $C_{10}$ monoglyceride, $C_{11}$ monoglyceride, $C_{12}$ monoglyceride, or $C_{13}$ monoglyceride, and
         (ii) at least one surfactant having an HLB value above about 8;
   (b) administering an effective amount of the water-in-oil microemulsion to the body of an animal, wherein the administration is parenterally, enterally, or via any other mucous membrane; and
   (c) achieving a therapeutically elective increase in the blood system of said animal of said biologically-active material.

17. The method of claim 16 wherein the active agent is a protein or a peptide.

18. The method of claim 16 wherein the administration is orally.

19. The method of claim 18 wherein the administration is rectally.

20. The method of any of the claims 18 or 19 further comprising converting the water-in-oil microemulsion to an oil-in-water emulsion after the administration step by the addition of aeueous body fluid.

21. The water-in-oil microemulsion composition of claim 3 wherein said biologically active material comprises heparin or its derivatives.

22. The water-in-oil microemulsion composition of claim 13 wherein said biologically active material comprises heparin or its derivatives.

* * * * *

UNITED STATES PATENT AND TRADEMARK OFFICE
CERTIFICATE OF CORRECTION

PATENT NO. : 5,688,761                                Page 1 of 2
DATED : November 18, 1997
INVENTOR(S) : Owen et al.

It is certified that error appears in the above-identified patent and that said Letters Patent is hereby corrected as shown below:

Column 1, line 49, please delete "systemby" and insert therefor --system by--.
Column 3, line 1, please delete "deliveredby" and insert therefor --delivered by--.
Column 4, line 60, please delete "Caprex" and insert therefor --Captex--.
Column 4, line 65, please delete "Caprex" and insert therefor --Captex--.
Column 6, line 36, please delete "replacedby" and insert therefor --replaced by--.
Column 7, line 26, please delete "Caprex" and insert therefor --Captex--.
Column 7, line 39, please delete "Caprex" and insert therefor --Captex--.
Column 8, line 47, please delete "Muls" and insert therefor --Huls--.
Column 10, line 27, please delete "TrP" and insert therefor --Trp--.
Column 15, line 65, please delete "Such" and insert therefor --such--.
Column 17, line 55, please delete "Caprex" and insert therefor --Captex--.
Column 20, line 15, please delete "salihe" and insert therefor --saline--.
Column 21, line 17, please delete "Caprex" and insert therefor --Captex--.
Column 23, line 47, please delete "microemUlsion" and insert therefor --microemulsion--.

UNITED STATES PATENT AND TRADEMARK OFFICE
CERTIFICATE OF CORRECTION

PATENT NO. : 5,688,761
DATED : November 18, 1997
INVENTOR(S) : Owen et al.

It is certified that error appears in the above-identified patent and that said Letters Patent is hereby corrected as shown below:

Column 23, line 57, please delete "Wherein" and insert therefor --wherein--.

Signed and Sealed this

Twenty-fourth Day of February, 1998

Attest:

BRUCE LEHMAN

Attesting Officer

Commissioner of Patents and Trademarks